United States Patent
Iaccino et al.

(10) Patent No.: US 10,155,703 B2
(45) Date of Patent: *Dec. 18, 2018

(54) PROCESSES AND SYSTEMS FOR CONVERTING HYDROCARBONS TO CYCLOPENTADIENE

(71) Applicant: ExxonMobil Chemical Patents Inc., Baytown, TX (US)

(72) Inventors: Larry L. Iaccino, Seabrook, TX (US); Romain O. V. Lemoine, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 76 days.

This patent is subject to a terminal disclaimer.

(21) Appl. No.: 15/288,439

(22) Filed: Oct. 7, 2016

(65) Prior Publication Data

US 2017/0121252 A1    May 4, 2017

Related U.S. Application Data

(60) Provisional application No. 62/250,682, filed on Nov. 4, 2015.

(51) Int. Cl.
| | |
|---|---|
| *C07C 5/327* | (2006.01) |
| *C07C 5/32* | (2006.01) |
| *C07C 5/333* | (2006.01) |
| *C07C 5/373* | (2006.01) |
| *B01J 29/44* | (2006.01) |

(Continued)

(52) U.S. Cl.
CPC ............... *C07C 5/373* (2013.01); *B01J 29/44* (2013.01); *B01J 29/63* (2013.01); *B01J 29/90* (2013.01); *C07C 2101/10* (2013.01); *C07C 2529/44* (2013.01); *C07C 2601/10* (2017.05); *Y02P 20/588* (2015.11)

(58) Field of Classification Search
CPC ............ C07C 5/327; C07C 5/32; C07C 5/333
USPC ........................................ 585/365, 366, 369
See application file for complete search history.

(56) References Cited

U.S. PATENT DOCUMENTS

| | | |
|---|---|---|
| 2,438,398 A | 3/1948 | Kennedy et al. |
| 2,438,399 A | 3/1948 | Kennedy et al. |

(Continued)

FOREIGN PATENT DOCUMENTS

| | | |
|---|---|---|
| DE | 2535809 | 3/1976 |
| EP | 0637578 | 4/1996 |
| WO | WO 89/04818 | 6/1989 |

OTHER PUBLICATIONS

U.S. Appl. No. 62/250,674, filed Nov. 4, 2015, Iaccino et al.

(Continued)

*Primary Examiner* — Thuan D Dang

(57) ABSTRACT

This invention relates to a process for converting acyclic $C_5$ hydrocarbons to cyclic $C_5$ compounds including cyclopentadiene in a reactor system, wherein the process comprises: providing to the reactor system a feedstock comprising acyclic $C_5$ hydrocarbons; providing to the reactor system a particulate material comprising a catalyst material; contacting the feedstock and the particulate material in at least one reaction zone under reaction conditions to convert at least a portion of the acyclic $C_5$ hydrocarbons to a first effluent comprising cyclopentadiene; wherein the feedstock flows co-current to a direction of a flow of the particulate material.

24 Claims, 5 Drawing Sheets

(51) Int. Cl.
  *B01J 29/63* (2006.01)
  *B01J 29/90* (2006.01)

(56) References Cited

U.S. PATENT DOCUMENTS

| | | | |
|---|---|---|---|
| 2,438,400 | A | 3/1948 | Hetzel et al. |
| 2,438,401 | A | 3/1948 | Kennedy et al. |
| 2,438,402 | A | 3/1948 | Kennedy et al. |
| 2,438,403 | A | 3/1948 | Kennedy et al. |
| 2,438,404 | A | 3/1948 | Hetzel et al. |
| 2,982,798 | A | 5/1961 | Hachmuth et al. |
| 3,953,368 | A | 4/1976 | Sinfelt |
| 4,229,602 | A | 10/1980 | Brinkmeyer et al. |
| 4,886,926 | A | 12/1989 | Dessau et al. |
| 5,192,728 | A | 3/1993 | Dessau et al. |
| 5,254,787 | A | 10/1993 | Dessau |
| 5,284,986 | A | 2/1994 | Dessau |
| 5,406,011 | A | 4/1995 | Radcliffe et al. |
| 5,510,557 | A | 4/1996 | Gartside et al. |
| 5,633,421 | A | 5/1997 | Iezzi et al. |
| 5,656,243 | A | 8/1997 | Luckenbach et al. |
| 7,589,246 | B2 | 9/2009 | Iaccino et al. |
| 7,951,341 | B2 | 5/2011 | Stewart et al. |
| 8,282,886 | B2 | 10/2012 | Glover et al. |
| 8,282,887 | B2 | 10/2012 | Myers et al. |
| 8,624,074 | B2 | 1/2014 | Towler et al. |
| 8,653,317 | B2 | 2/2014 | Pierce et al. |
| 2010/0234657 | A1 | 9/2010 | Takamatsu et al. |
| 2014/0140895 | A1 | 5/2014 | Davydov et al. |
| 2014/0142362 | A1 | 5/2014 | Davydov et al. |
| 2015/0038757 | A1 | 2/2015 | Spieker et al. |
| 2017/0121249 | A1 | 5/2017 | Iaccino et al. |
| 2017/0121250 | A1 | 5/2017 | Iaccino et al. |
| 2017/0121251 | A1 | 5/2017 | Iaccino et al. |
| 2017/0121255 | A1 | 5/2017 | Iaccino et al. |

OTHER PUBLICATIONS

U.S. Appl. No. 62/250,680, filed Nov. 4, 2015, Iaccino et al.
U.S. Appl. No. 62/250,693, filed Nov. 4, 2015, Iaccino et al.
U.S. Appl. No. 62/250,677, filed Nov. 4, 2015, Iaccino et al.
U.S. Appl. No. 62/250,682, filed Nov. 4, 2015, Iaccino et al.
U.S. Appl. No. 62/250,697, filed Nov. 4, 2015, Iaccino.
Fel'dblyum, V.S., et al. "*Cyclization and Dehydrocyclization of $C_5$ Hydrocarbons over Platinum Nanocatalysts and in the Presence of Hydrogen Sulfide,*" Doklady Chemistry, 2009, vol. 424, Part 2, pp. 27-30.
Geldart, D. "*Types of Gas Fluidization,*" Powder Technology, 1973, vol. 7, pp. 285-292.
Kanazirev, V., et al. "*Conversion of $C_8$ Aromatics and n-Pentane Over $Ga_2O_3$/HZSM-5 Mechanically Mixed Catalysts,*" Catalysis Letters, 1991, vol. 9, pp. 35-42.
Kennedy, R.M. et al., "*Formation of Cyclopentadiene from 1,3-Pentadiene,*" Industrial and Engineering Chemistry, 1950, vol. 42, No. 3, pp. 547-552.
Kunii, D. et al., "*Fluidization Engineering,*" $2^{nd}$ Edition Butterworth-Heinemann, Boston, 1991, Chapter 3, pp. 61-94.
Li, X., et al. "*Catalytic Dehydroisomerization of n-alkanes to Isoalkenes,*" Journal of Catalysis, 2008, vol. 255, pp. 134-137.
Lopez, C.M., et al. "*n-Pentane Hydroisomerization on Pt Containing HZSM-5, HBEA and SAPO-11,*" Catalysis Letters, 2008, vol. 122, pp. 267-273.
Marcinkowski, T.E., "*Isomerization and Dehydrocyclization of 1,3-Pentadiene,*" Retrospective Theses and Dissertations, 1979, Paper 433, pp. 1-110.
Sattler, et al. "*Catalytic Dehydrogenation of Light Alkanes on Metals and Metal Oxides,*" Chemical Reviews, 2014, vol. 114, No. 20, pp. 10613-10653.
Stewart, P.S.B., et al. "*Slug Flow in Fluidised Beds,*" Powder Technology, 1967, vol. 1, p. 61-80.
Vora, B.V., "*Development of Dehydrogenation Catalysts and Processes,*" Topics in Catalysis, 2012, vol. 55, pp. 1297-1308.
Walas, S., et al. "*Chemical Process Equipment,*" Revised Second Edition, Elsevier, Inc., 2010, Chapter 6, pp. 83-118.
Xu, Y., et al., "*Methane Activation Without Using Oxidants Over Mo/HZSM-5 Zeolite Catalysts,*" Catalysis Letter, 1995, vol. 30, pp. 135-149.
U.S. Appl. No. 15/288,412, filed Oct. 7, 2016, Iaccino et al.
Bricker, J.C., "*Advanced Catalytic Dehydrogenation Technologies for Production of Olefins*", Topics in Catalysis, vol. 55, pp. 1309-1314, 2012.

PROCESSES AND SYSTEMS FOR CONVERTING HYDROCARBONS TO CYCLOPENTADIENE

CROSS REFERENCE TO RELATED APPLICATIONS

This invention claims priority to and the benefit of U.S. Ser. No. 62/250,682, filed Nov. 4, 2015. This application relates to U.S. Ser. No. 62/250,680, filed Nov. 4, 2015, U.S. Ser. No. 62/250,677, filed Nov. 4, 2015, and U.S. Ser. No. 62/250,697, filed Nov. 4, 2015.

FIELD OF THE INVENTION

This invention relates to reactors useful for processes for the conversion of acyclic $C_5$ feedstock to a product comprising cyclic $C_5$ compounds.

BACKGROUND OF THE INVENTION

Cyclopentadiene (CPD) and its dimer dicyclopentadiene (DCPD) are highly desired raw materials used throughout the chemical industry in a wide range of products, such as, polymeric materials, polyester resins, synthetic rubbers, solvents, fuels, fuel additives, etc. Cyclopentadiene is currently a minor byproduct of liquid fed steam cracking (for example, naphtha, and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. Co-production of other cyclic $C_5$'s is also desirable. Cyclopentane and cyclopentene can have high value as solvents while cyclopentene may be used as a comonomer to produce polymers and as a starting material for other high value chemicals.

It would be advantageous to be able to produce cyclic $C_5$ compounds, including CPD, as the primary product from plentiful $C_5$ feedstock using a catalyst system to produce CPD while minimizing production of light ($C_{4-}$) byproducts. While lower hydrogen content (for example, cyclics, alkenes, and dialkenes) could be preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil, as well as reduced use in motor fuels due to stringent environmental regulations. $C_5$ feedstock may also be derived from bio-feeds.

Various catalytic dehydrogenation technologies are currently used to produce mono- and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization, which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_2$-$C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. No. 2,438,398; U.S. Pat. No. 2,438,399; U.S. Pat. No. 2,438,400; U.S. Pat. No. 2,438,401; U.S. Pat. No. 2,438,402; U.S. Pat. No. 2,438,403; and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," *Industrial & Engineering Chemistry*, vol. 42, pp. 547-552, 1950.

Fel'dblyum et al., in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al., in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites including H-ZSM-5. At intermediate temperatures (250° C.-400° C.), they reported efficient hydroisomerization of n-pentane on the Pt-zeolites with no discussion of cyclopentene formation. It is desirable to avoid this deleterious chemistry as branched $C_5$ do not produce cyclic $C_5$ as efficiently as linear $C_5$, as discussed above.

Li et al., in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic $C_5$ hydrocarbons, which are desirable as feedstock because they are plentiful and low cost.

Further, many challenges exist in designing an on-purpose CPD production process. For example, the reaction converting $C_5$ hydrocarbons to CPD is extremely endothermic and is favored by low pressure and high temperature, but significant cracking of n-pentane and other $C_5$ hydrocarbons can occur at relatively low temperatures (e.g., 450° C.-500° C.). Further challenges include loss of catalyst activity due to coking during the process and further processing needed to remove coke from the catalyst, and the inability to use oxygen-containing gas to directly provide heat input to the reactor without damaging the catalyst.

Hence, there remains a need for a process to convert acyclic $C_5$ feedstock to non-aromatic, cyclic $C_5$ hydrocarbon, namely cyclopentadiene, preferably at commercial rates and conditions. Further, there is a need for a catalytic process targeted for the production of cyclopentadiene, which generates cyclopentadiene in high yield from plentiful $C_5$ feedstocks without excessive production of $C_{4-}$ cracked products and with acceptable catalyst aging properties. Additionally, there is a need for processes and systems for on-purpose CPD production from acyclic $C_5$ hydrocarbons, which address the above-described challenges.

SUMMARY OF THE INVENTION

In one aspect, this invention relates to a process for converting acyclic $C_5$ hydrocarbons to cyclic C5 compounds, including cyclopentadiene in a reactor system, wherein the process comprises: providing to the reactor system a feedstock comprising acyclic $C_5$ hydrocarbons; providing to the reactor system a particulate material comprising a catalyst material; contacting the feedstock and the particulate material in at least one reaction zone under reaction conditions to convert at least a portion of the acyclic $C_5$ hydrocarbons to a first effluent comprising cyclopentadiene; wherein the feedstock flows co-current to a direction of a flow of the particulate material.

In another aspect, this invention also relates to a reaction system for converting acyclic $C_5$ hydrocarbons to cyclic $C_5$ compounds including cyclopentadiene, wherein the reaction system comprises: a feedstock stream comprising acyclic $C_5$ hydrocarbons; a first effluent stream comprising cyclopentadiene; at least one catalyst stream comprising a particulate material comprising a catalyst material; at least one spent catalyst stream comprising spent catalyst material; at least one reactor operated under reaction conditions to convert at least a portion of the acyclic $C_5$ hydrocarbons to cyclopentadiene; and wherein the at least one reactor comprises: a feedstock inlet for providing the feedstock stream to the reaction system; at least one catalyst inlet for providing the at least one catalyst stream to the reaction system; and an effluent outlet for removal of the first effluent stream and the at least one spent catalyst stream; wherein the feedstock stream in the reactor flows co-current to a direction of a flow of the at least one catalyst stream in the reactor.

DETAILED DESCRIPTION OF THE INVENTION

I. Definitions

Figure 1:
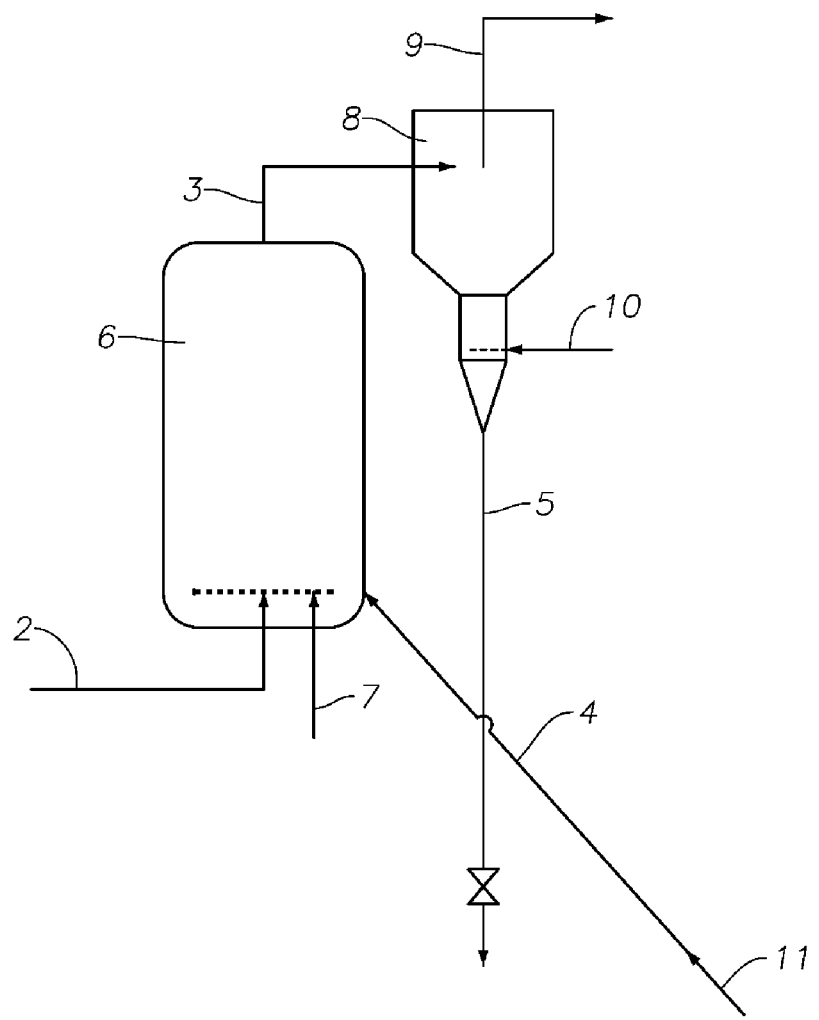
FIG. 1 is a diagram of a reactor system according to an embodiment of the invention.

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

As used herein, the term "about" refers to a range of values of plus or minus 10% of a specified value. For example, the phrase "about 200" includes plus or minus 10% of 200, or from 180 to 220.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene, and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, Ni, Pd, and Pt.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

As used herein, the term "oxygen-containing" or "oxygen-containing compound" means oxygen and compounds containing oxygen, including but not limited to, $O_2$, $CO_2$, CO, $H_2O$, and oxygen-containing hydrocarbons such as alcohols, esters, ethers, etc.

The term "constraint index" is defined in U.S. Pat. No. 3,972,832 and U.S. Pat. No. 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types," Fifth edition, 2001, the entire content of which is incorporated herein by reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "carbon selectivity" means the moles of carbon in the respective cyclic $C_5$, CPD, $C_1$, and $C_{2-4}$ formed divided by total moles of carbon in the pentane converted. The phrase "a carbon selectivity to cyclic $C_5$ of at least 30%" means that 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "reactor system" refers to a system including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reaction zones across multiple reactors. In other words and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes, including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where Umf is minimum fluidizing velocity, Umb is minimum bubbling velocity, Uc is the velocity at which fluctuation in pressure peaks, and tr is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991, and Walas, S. M., Chapter 6 of *Chemical Process Equipment*, Revised $2^{nd}$ Edition, Butterworth-Heinemann, Boston, 2010, which are incorporated herein by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity, while maintaining a gradient in gas and/or solid property (such as, temperature, gas, or solid composition, etc.), axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991, and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, 2nd Edition, Butterworth-Heinemann, Boston, 1991, and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor, such as a circulating fluidized bed reactor, may be operated as a riser reactor.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

II. Acyclic $C_5$ Conversion Process

The first aspect of the invention is a process for conversion of an acyclic $C_5$ feedstock to a product comprising cyclic $C_5$ compounds (e.g., cyclopentadiene). The process comprises the steps of contacting said feedstock and, optionally, hydrogen under acyclic $C_5$ conversion conditions in the presence of one or more catalyst compositions, including but not limited to the catalyst compositions described herein, to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least about 20 wt %, or 30 wt %, or 40 wt %, or 70 wt % cyclopentadiene, or in the range of from about 10 wt % to about 80 wt %, alternately 20 wt % to 70 wt %.

In one or more embodiments, the acyclic $C_5$ conversion conditions include at least a temperature, a partial pressure, and a weight hourly space velocity (WHSV). The temperature is in the range of about 400° C. to about 700° C., or in the range from about 450° C. to about 650° C., preferably, in the range from about 500° C. to about 600° C. The partial pressure of n-pentane is in the range of about 3 to about 100 psia at the reactor inlet, or in the range from about 3 to about 50 psia, preferably, in the range from about 3 psia to about 20 psia. The weight hourly space velocity is in the range from about 1 to about 50 hr$^{-1}$, or in the range from about 1 to about 20 hr$^{-1}$. Such conditions include a molar ratio of the optional hydrogen co-feed to the acyclic $C_5$ feedstock in the range of about 0 to 3, or in the range from about 1 to about 2. Such conditions may also include co-feed $C_1$-$C_4$ hydrocarbons with the acyclic $C_5$ feed. Preferably, co-feed (if present), whether comprising hydrogen, $C_1$-$C_4$ hydrocarbons or both, is substantially free of oxygen-containing compounds. "Substantially free" used in this context means the co-feed comprises less than about 1.0 wt %, based upon the weight of the co-feed, e.g., less than about 0.1 wt %, less than about 0.01 wt %, less than about 0.001 wt %, less than about 0.0001 wt %, less than about 0.00001 wt % of oxygen-containing compounds.

In one or more embodiments, this invention relates to a process for conversion of n-pentane to cyclopentadiene comprising the steps of contacting n-pentane and, optionally, hydrogen (if present, typically H$_2$ is present at a ratio to n-pentane of 0.01 to 3.0) with one or more catalyst compositions, including but not limited to the catalyst compositions described herein, to form cyclopentadiene at a temperature of 400° C. to 700° C., an n-pentane partial pressure of 3 to about 100 psia at the reactor inlet, and a weight hourly space velocity of 1 to about 50 hr$^{-1}$.

In one embodiment, this invention relates to a process for converting $C_5$ hydrocarbons to cyclopentadiene in a reactor system, wherein the process comprises: providing to the reactor system a feedstock comprising $C_5$ hydrocarbons; providing to the reactor system a particulate material comprising a catalyst material; contacting the feedstock and the particulate material in at least one reaction zone under reaction conditions to convert at least a portion of the $C_5$ hydrocarbons to a first effluent comprising cyclopentadiene; wherein the feedstock flows co-current to a direction of a flow of the particulate material.

A. Feedstock

In the process, a feedstock comprising $C_5$ hydrocarbons, preferably an acyclic $C_5$ feedstock is provided to a reaction system along with a particulate material comprising a catalyst material. An acyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene, and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ feedstock, optionally, does not comprise $C_6$ aromatic compounds, such as benzene, preferably $C_6$ aromatic compounds are present at less than 5 wt %, preferably less than 1 wt %, preferably present at less than 0.01 wt %, preferably at 0 wt %.

The acyclic $C_5$ feedstock, optionally, does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic $C_5$ feedstock, optionally, does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock, optionally, does not comprise $C_{6+}$ compounds, preferably $C_{6+}$ compounds are present at less than 5 wt %, preferably less than 1 wt %, preferably present at less than 0.01 wt %, preferably at 0 wt %.

Preferably, the $C_5$ feedstock is substantially free of oxygen-containing compounds. "Substantially free" used in this context means the feedstock comprises less than about 1.0 wt %, based upon the weight of the feed, e.g., less than about 0.1 wt %, less than about 0.01 wt %, less than about 0.001 wt %, less than about 0.0001 wt %, less than about 0.00001 wt % oxygen-containing compounds.

Preferably, an amount of the $C_5$ hydrocarbons (e.g., acyclic $C_5$ hydrocarbons) in the feedstock converted to cyclopentadiene is ≥about 5.0 wt %, ≥about 10.0 wt %, ≥about 20.0 wt %, ≥about 30.0 wt %, ≥about 40.0 wt %, ≥about 50.0 wt %, ≥about 60.0 wt %, ≥about 70.0 wt %, ≥about 80.0 wt %, or ≥about 90.0 wt %. Preferably, at least about 30.0 wt % or at least about 60.0 wt % of the $C_5$ hydrocarbons (e.g., acyclic $C_5$ hydrocarbons) is converted to cyclopentadiene. Ranges expressly disclosed include combinations of any of the above-enumerated values; e.g., about 5.0% to about 90.0 wt %, about 10.0 wt % to about 80.0 wt %, about 20.0 wt % to about 70.0 wt %, about 20.0 wt % to about 60.0 wt %, etc. Preferably, about 5.0 wt % to about 100.0 wt % of the $C_5$ hydrocarbons (e.g., acyclic $C_5$ hydrocarbons) is converted to cyclopentadiene, more preferably about 10.0 wt % to about 90.0 wt %, more preferably about 20.0 wt % to about 80.0 wt %, about 30.0 wt % to about 70.0 wt %, about 40.0 wt % to about 60.0 wt %.

Preferably, a hydrogen co-feedstock comprising hydrogen and, optionally, light hydrocarbons, such as $C_1$-$C_4$ hydrocarbons, is also fed into the first reactor. Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles. $C_1$-$C_4$ hydrocarbons may also be co-fed with the $C_5$.

B. Reaction Zone

The feedstock is fed into a reactor system and contacted with a particulate material comprising a catalyst material in the at least one reaction zone under reaction conditions to convert at least a portion of the $C_5$ hydrocarbons (e.g., acyclic $C_5$ hydrocarbons) to a first effluent comprising cyclopentadiene. The at least one reaction zone may be a circulating fluidized bed reactor. Further, the circulating fluidized bed reactor may be operated in a fast-fluidization regime or pneumatic conveying fluidization regime, as described in the above Kunii and Walas publications. In other words, the circulating fluidized bed reactor may be operated as a riser reactor.

The at least one reaction zone may include at least one internal structure, preferably a plurality of internal structures (e.g., 2, 3, 4, 5, 6, 7, 8, 9, 10, 15, 20, 30, 40, 50, etc.), to influence a velocity vector of the particulate material. Further, the internal structure(s) can ensure movement of particulate material to reduce the degree of back-mixing. Particularly, the at least one reaction zone may include a plurality of internal structures. Examples of suitable internal structures include a plurality of vertical baffles including baffles shaped as radial fins or as annular cylinders, sheds, trays, tubes, rods, and/or distributors.

The at least one reaction zone is operated under reaction conditions sufficient to convert the feedstock (e.g., acyclic $C_5$ hydrocarbons) to cyclopentadiene. Preferably, the feedstock (e.g., acyclic $C_5$ hydrocarbons) may be fed to the reaction system at a weight hourly space velocity (WHSV, mass of acyclic $C_5$ hydrocarbons/mass of catalyst/hour) in the range of from about 1.0 to about 1000.0 $hr^{-1}$. The WHSV may be about 1.0 to about 900.0 $hr^{-1}$, about 1.0 to about 800.0 $hr^{-1}$, about 1.0 to about 700.0 $hr^{-1}$, about 1.0 to about 600.0 $hr^{-1}$, about 1.0 to about 500.0 $hr^1$, about 1.0 to about 400.0 $hr^1$, about 1.0 to about 300.0 $hr^{-1}$, about 1.0 to about 200.0 $hr^{-1}$, about 1.0 to about 100.0 $hr^{-1}$, about 1.0 to about 90.0 $hr^{-1}$, about 1.0 to about 80.0 $hr^{-1}$, about 1.0 to about 70.0 $hr^{-1}$, about 1.0 to about 60.0 $hr^{-1}$, about 1.0 to about 50.0 $hr^{-1}$, about 1.0 to about 40.0 $hr^{-1}$, about 1.0 to about 30.0 $hr^{-1}$, about 1.0 to about 20.0 $hr^{-1}$, about 1.0 to about 10.0 $hr^{-1}$, about 1.0 to about 5.0 $hr^{-1}$, about 2.0 to about 1000.0 $hr^{-1}$, about 2.0 to about 900.0 $hr^{-1}$, about 2.0 to about 800.0 $hr^{-1}$, about 2.0 to about 700.0 $hr^{-1}$, about 2.0 to about 600.0 $hr^{-1}$, about 2.0 to about 500.0 $hr^{-1}$, about 2.0 to about 400.0 $hr^{-1}$, about 2.0 to about 300.0 $hr^{-1}$, about 2.0 to about 200.0 $hr^{-1}$, about 2.0 to about 100.0 $hr^{-1}$, about 2.0 to about 90.0 $hr^{-1}$, about 2.0 to about 80.0 $hr^{-1}$, about 2.0 to about 70.0 $hr^{-1}$, about 2.0 to about 60.0 $hr^{-1}$, about 2.0 to about 50.0 $hr^{-1}$, about 2.0 to about 40.0 $hr^{-1}$, about 2.0 to about 30.0 $hr^{-1}$, about 2.0 to about 20.0 $hr^{-1}$, about 2.0 to about 10.0 $hr^{-1}$, and about 2.0 to about 5.0 $hr^{-1}$. Preferably, the WHSV is about 1.0 to about 100.0 $hr^{-1}$, more preferably about 1.0 to about 60.0 $hr^{-1}$, more preferably about 2.0 to about 40.0 $hr^{-1}$, more preferably about 2.0 to about 20.0 $hr^{-1}$.

Additionally, it is preferable that a substantially isothermal temperature profile be maintained in the at least one reaction zone. As used herein, "isothermal temperature profile" of the at least one reaction zone means that temperatures of the at least one reaction zone is kept essentially constant, e.g., at the same temperature or within the same narrow temperature range wherein the difference between an upper temperature and a lower temperature is no more than about 40° C.; more preferably no more than about 20° C. Preferably, the isothermal temperature profile is one where the reactor inlet temperature is within about 40° C. of the reactor outlet temperature, alternately within about 20° C., alternately within about 10° C., alternately within about 5° C., alternately the reactor inlet temperature is the same as the reactor outlet temperature. Alternately, the isothermal temperature profile is one where the reactor inlet temperature is within about 20% of the reactor outlet temperature, alternately within about 10%, alternately within about 5%, alternately within about 1%.

Preferably, the isothermal temperature profile is one where the temperature along the length of the reaction zone does not vary by more than about 40° C. as compared to reactor inlet temperature, alternately not more than about 20° C., alternately not more than about 10° C., alternately not more than about 5° C. Alternately, the isothermal temperature profile is one where the temperature along the length of the reaction zone is within about 20% of the reactor inlet temperature, alternately within about 10%, alternately within about 5%, alternately within about 1% of the reactor inlet temperature. An advantage of maintaining an inverse temperature profile may be an increased product yield due to a reduction in cracking of the acyclic $C_5$ hydrocarbons to lighter hydrocarbon ($C_{4-}$) byproducts.

Thus, the temperature of the feedstock (e.g., acyclic $C_5$ hydrocarbons) entering the reactor system at a feedstock inlet may be ≤about 700° C., ≤about 675° C., ≤about 650° C., ≤about 625° C., ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C. or ≤about 200° C. Preferably, the temperature of the feedstock (e.g., acyclic $C_5$ hydrocarbons) entering the reactor system is ≤about 575° C., more preferably ≤about 550° C., more preferably ≤about 525° C., more preferably ≤about 500° C. Ranges of temperatures expressly disclosed include combinations of any of the above-enumerated values, e.g., about 200° C. to about 700° C., about 250° C. to about 600° C., about 350° C. to about 650° C., about 375° C. to about 500° C., etc. Preferably, the temperature of the feedstock (e.g., acyclic $C_5$ hydrocarbons) entering the reactor system is about 200° C. to about 700° C., more preferably about 300° C. to about 600° C., more preferably about 400° C. to about 550° C., more preferably about 475° C. to about 525° C. Providing the feedstock (e.g., acyclic $C_5$ hydrocarbons) at the above-described temperatures may advantageously minimize undesirable cracking of the $C_5$ hydrocarbons (e.g., acyclic $C_5$ hydrocarbons) before they can react with the catalyst material.

Additionally, the temperature of a first effluent exiting the at least one reaction zone at an effluent outlet may be ≥about 400° C., ≥about 425° C., ≥about 450° C., ≥about 475° C., ≥about 500° C., ≥about 525° C., ≥about 550° C., ≥about 575° C., ≥about 600° C., ≥about 625° C., ≥about 650° C., ≥about 675° C., or ≥about 700° C. Preferably, the temperature of a first effluent exiting the at least one reaction zone is ≥about 550° C., more preferably ≥about 575° C., more preferably ≥about 600° C. Ranges of temperatures expressly disclosed include combinations of any of the above-enumerated values, e.g., about 400° C. to about 700° C., about 475° C. to about 675° C., about 525° C. to about 650° C., about 550° C. to about 600° C., etc. Preferably, the temperature of a first effluent exiting the at least one reaction zone is about 475° C. to about 700° C., more preferably about 500° C. to about 650° C., more preferably about 550° C. to about 625° C.

Additionally or alternatively, reaction conditions in the at least one reaction zone may include a temperature of ≥about 300° C., ≥about 325° C., ≥about 350° C., ≥about 375° C., ≥about 400° C., ≥about 425° C., ≥about 450° C., ≥about 475° C., ≥about 500° C., ≥about 525° C., ≥about 550° C., ≥about 575° C., ≥about 600° C., ≥about 625° C., ≥about 650° C., ≥about 675° C., or ≥about 700° C. Additionally or alternatively, the temperature may be ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 625° C., ≤about 650° C., ≤about 675° C., or ≤about 700° C. Ranges of temperatures expressly disclosed include combinations of any of the above-enumerated values, e.g., about 300° C. to about 700° C., about 350° C. to about 675° C., and about 400° C. to about 600° C., etc. Preferably, the temperature may be about 325° C. to about 700° C., more preferably about 400° C. to about 650° C., more preferably about 350° C. to about 650° C., more preferably about 450° C. to about 625° C. Optionally, the at least one reaction zone may include one or more heating devices in order to maintain a temperature therein. Examples of suitable heating devices known in the art include, but are not limited to a fired tube, a heated coil with a high temperature heat transfer fluid, an electrical heater, and/or a microwave emitter. As used herein, "coil" refers to a structure placed within a vessel through which a heat transfer fluid flows to transfer heat to the vessel contents. A coil may have any suitable cross-sectional shape and may be straight, include u-bends, include loops, etc.

Additionally or alternatively, reaction conditions in the at least one reaction zone may include a pressure of ≤about 1.0 psia, ≤about 2.0 psia, ≤about 3.0 psia, ≤about 4.0, ≤about 5.0 psia, ≤about 10.0 psia, ≤about 15.0 psia, ≤about 20.0 psia, ≤about 25.0 psia, ≤about 30.0 psia, ≤about 35.0 psia, ≤about 40.0 psia, ≤about 45.0 psia, ≤about 50.0 psia, ≤about 55.0 psia, ≤about 60.0 psia, ≤about 65.0 psia, ≤about 70.0 psia, ≤about 75.0 psia, ≤about 80.0 psia, ≤about 85.0 psia, ≤about 90.0 psia, ≤about 95.0 psia, ≤about 100.0 psia, ≤about 125.0 psia, ≤about 150.0 psia, ≤about 175.0 psia, or ≤about 200.0 psia. Additionally or alternatively, the pressure may be ≥about 1.0 psia, ≥about 2.0 psia, ≥about 3.0 psia, ≥about 4.0 psia, ≥about 5.0 psia, ≥about 10.0 psia, ≥about 15.0 psia, ≥about 20.0 psia, ≥about 25.0 psia, ≥about 30.0 psia, ≥about 35.0 psia, ≥about 40.0 psia, ≥about 45.0 psia, ≥about 50.0 psia, ≥about 55.0 psia, ≥about 60.0 psia, ≥about 65.0 psia, ≥about 70.0 psia, ≥about 75.0 psia, ≥about 80.0 psia, ≥about 85.0 psia, ≥about 90.0 psia, ≥about 95.0 psia, ≥about 100.0 psia, ≥about 125.0 psia, ≥about 150.0 psia, ≥about 175.0 psia, or ≥about 200.0 psia. Ranges and combinations of temperatures and pressures expressly disclosed include combinations of any of the above-enumerated values, e.g., about 1.0 psia to about 200.0 psia, about 2.0 psia to about 175.0 psia, about 5.0 psia to about 95.0 psia, etc. Preferably, the pressure may be about 1.0 psia to about 150.0 psia, more preferably about 2.0 psia to about 100.0 psia, more preferably about 3.0 psia to about 80.0 psia.

Additionally or alternatively, a pressure substantially at a feedstock inlet and/or substantially at an effluent outlet may be ≥about 0.5 psia, ≥about 1.0 psia, ≥about 2.0 psia, ≥about 3.0 psia, ≥about 4.0 psia, ≥about 5.0 psia, ≥about 10.0 psia, ≥about 14.0 psia, ≥about 15.0 psia, ≥about 20.0 psia, ≥about 24.0 psia, ≥about 25.0 psia, ≥about 30.0 psia, ≥about 35.0 psia, ≥about 40.0 psia, ≥about 45.0 psia, or ≥about 50.0 psia. As understood herein, "at a feedstock inlet," "at an inlet," "at an effluent outlet" and "at an outlet" includes the space in and substantially around the inlet and/or outlet. Additionally or alternatively, a pressure substantially at a feedstock inlet and/or substantially at an effluent outlet may be ≤about 0.5 psia, ≤about 1.0 psia, ≤about 2.0 psia, ≤about 3.0 psia, ≤about 4.0 psia, ≤about 5.0 psia, ≤about 10.0 psia, ≤about 14.0 psia, ≤about 15.0 psia, ≤about 20.0 psia, ≤about 24.0 psia, ≤about 25.0 psia, ≤about 30.0 psia, ≤about 35.0 psia, ≤about 40.0 psia, ≤about 45.0 psia, or ≤about 50.0 psia. Ranges of pressures expressly disclosed include combinations of any of the above-enumerated values, e.g., about 0.5 psia to about 50.0 psia, about 5.0 psia to about 35.0 psia, about 1.0 psia to about 15.0 psia, etc. In particular, the pressure substantially at feedstock inlet and/or substantially at an effluent outlet may be about 1.0 psia to about 20.0 psia, preferably about 4.0 psia to about 14.0 psia, more preferably about 4.0 psia to about 10.0 psia.

Additionally or alternatively, a delta pressure across the at least one reaction zone (pressure at feedstock inlet minus pressure at effluent outlet) may be low due to the fluidization regime, e.g., at least about 0.1 psi, at least about 0.2 psi, at least about 0.3 psi, at least about 0.4 psi, at least about 0.5 psi, at least about 0.6 psi, at least about 0.7 psi, at least about 0.8 psi, at least about 0.9 psi, at least about 1.0 psi, at least about 1.5 psi, at least about 2.0 psi, at least about 4.0 psi, at least about 6.0 psi, at least about 8.0 psi, at least about 10.0 psi, at least about 12.0 psi, at least about 15.0 psi, or at least about 20.0 psi. Preferably, the delta pressure across the at least one reaction zone is between about 0.1 to about 20.0 psi, more preferably about 0.1 to about 15.0 psi, more preferably about 0.1 to about 10.0 psi, more preferably about 0.2 to about 1.5 psi.

Additionally or alternatively, a stream comprising hydrogen may be fed to the at least one reaction zone. Such a stream comprising hydrogen may be introduced into the at least one reaction zone in order to minimize production of coke material on the particulate material and/or to fluidize the particulate material in the at least one reaction zone. Such a stream comprising hydrogen may contain light hydrocarbons (e.g., $C_1$-$C_4$); preferably the content of light hydrocarbons is less than about 50 mol %, less than about 40 mol %, less than about 30 mol %, less than about 20 mol %, less than about 10 mol %, less than about 5 mol %, less than about 1 mol %. Preferably, the stream comprising hydrogen is substantially free of oxygen, e.g., less than about 1.0 wt %, less than about 0.1 wt %, less than about 0.01 wt %, less than about 0.001 wt %, less than about 0.0001 wt %, less than about 0.00001 wt %, etc.

C. Particulate Material

A particulate material comprising a catalyst material (catalyst composition) is provided to the reaction system for promoting conversion of the $C_5$ hydrocarbons (e.g., acyclic $C_5$ hydrocarbons) to cyclopentadiene. Preferably, the feedstock flows in a direction co-current to a direction of a flow of the particulate material.

Catalyst compositions useful herein include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework. Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from Groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11, or 13 metal) greater than about 3, or greater than about 25, or greater than about 50, or greater than about 100, or greater than about 400, or in the range from about 100 to about 2,000, or from about 100 to about 1,500, or from about 50 to about 2,000, or from about 50 to about 1,200.

In one or more embodiments, the crystalline aluminosilicate has an $SiO_2/Al_2O_3$ molar ratio greater than about 3, or greater than about 25, or greater than about 50, or greater than about 100, or greater than about 400, or in the range from about 100 to about 400, or from about 100 to about 500, or from about 25 to about 2,000, or from about 50 to about 1,500, or from about 100 to about 1,200, or from about 100 to about 1,000.

In another embodiment of the invention, the microporous crystalline metallosilicate (such as an aluminosilicate) is combined with a Group 10 metal or metal compound, and, optionally, one, two, three, or more Group 1, 2, or 11 metals or metal compounds.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition.

In one or more embodiments, the Group 10 content is in the range from about 0.005 wt % to about 10 wt %, or from about 0.005 wt % up to about 1.5 wt %, based on the weight of the catalyst composition.

In one or more embodiments, the Group 1 alkali metal includes, or is selected from the group consisting of, Li, Na, K, Rb, Cs, and mixtures of two or more thereof, preferably Na.

In one or more embodiments, the Group 2 alkaline earth metal is selected from the group consisting of Be, Mg, Ca, Sr, Ba, and mixtures of two or more thereof.

In one or more embodiments, the Group 1 alkali metal is present as an oxide and the metal is selected from the group consisting of Li, Na, K, Rb, Cs, and mixtures of two or more thereof. In one or more embodiments, the Group 2 alkaline earth metal is present as an oxide and the metal is selected from the group consisting of Be, magnesium, calcium, Sr, Ba, and mixtures of two or more thereof. In one or more embodiments, the Group 1 alkali metal is present as an oxide and the metal is selected from the group consisting of Li, Na, K, Rb, Cs, and mixtures of two or more thereof and the Group 2 alkaline earth metal is present as an oxide and the metal is selected from the group consisting of Be, magnesium, calcium, Sr, Ba, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15. Alpha Value is determined as described in U.S. Pat. No. 3,354,078; The Journal of Catalysis, v. 4, p. 527, (1965); v. 6, p. 278, (1966); and v. 61, p. 395, (1980) using a constant temperature of 538° C. and a variable flow rate, as described in detail in The Journal of Catalysis, v. 61, p. 395, (1980).

In one or more embodiments of aluminosilicates, the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 alkaline earth metal is present as an oxide and the metal is selected from the group consisting of gold, silver, and copper, and mixtures of two or more thereof.

In one or more embodiments, the use of any one of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions of an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 $hr^{-1}$.

In one or more embodiments, the use of any one of the catalyst compositions of this invention provides a carbon selectivity to cyclic $C_5$ compounds of at least about 30%, or at least about 40%, or at least about 50%, or in the range from about 30% to about 80%, under acyclic $C_5$ conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic $C_5$ conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^-$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and, more usually, particularly when the composite is prepared in the form of beads, extrudates, pills, oil drop formed particles, spray dried particles, etc., in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques, including high pressure hydrogen treatment and combustion of coke on the catalyst compositions with an oxygen-containing gas, such as air or $O_2$.

Useful catalyst compositions comprise a crystalline aluminosilicate or ferrosilicate, which is optionally combined with one, two, or more additional metals or metal compounds. Preferred combinations include:

1) a crystalline aluminosilicate (such as ZSM-5 or Zeolite L) combined with a Group 10 metal (such as Pt), a Group 1 alkali metal (such as sodium or potassium), and/or a Group 2 alkaline earth metal;

2) a crystalline aluminosilicate (such as ZSM-5 or Zeolite L) combined with a Group 10 metal (such as Pt) and a Group 1 alkali metal (such as sodium or potassium);

3) a crystalline aluminosilicate (such as a ferrosilicate or an iron treated ZSM-5) combined with a Group 10 metal (such as Pt) and a Group 1 alkali metal (such as sodium or potassium);

4) a crystalline aluminosilicate (Zeolite L) combined with a Group 10 metal (such as Pt) and a Group 1 alkali metal (such as potassium); and 5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as Li, Na, K, Rb, and/or Cs silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948, or DAVISON 955 (Davison Chemical Division of W. R. Grace and Company).

Catalyst composition shape and design are preferably configured to minimize pressure drop, increase heat transfer, and minimize mass transport phenomena. Suitable catalyst shape and design are described in WO 2014/053553, which is incorporated by reference in its entirety. The catalyst composition may be an extrudate with a diameter of 2 mm to 20 mm. Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled.

For more information on useful catalyst compositions, please see applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015, which are incorporated by reference herein.

Preferably, the catalyst material comprises platinum on ZSM-5, platinum on zeolite L, and/or platinum on silica.

Suitable amounts of catalyst material in the particulate material may be ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt %, or about 100.0 wt %. Additionally or alternatively, the particulate material may comprise the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, or ≥about 95.0 wt %. Preferably, the particulate material may comprise ≥about 30.0 wt % catalyst material. Ranges expressly disclosed include combinations of any of the above-enumerated values; e.g., about 1.0 wt % to about 100.0 wt %, about 5.0 wt % to about 100.0 wt %, about 10.0 wt % to about 90.0 wt %, about 20.0 wt % to about 80.0 wt %, etc. Preferably, the particulate material may comprise the catalyst material in an amount of about 1.0 wt % to about 100.0 wt %, more preferably about 5.0 wt % to about 100.0 wt %, more preferably about 25.0 wt % to about 100.0 wt %, more preferably about 50.0 wt % to about 100.0 wt %, more preferably about 70.0 wt % to about 100.0 wt %.

In various aspects, the particulate material may further comprise an inert material. As referred to herein, the inert material is understood to include materials which promote a negligible amount (e.g., ≤about 3%, ≤about 2%, ≤about 1%, etc.) of conversion of the feedstock, intermediate products, or final products under the reaction conditions described herein. The catalyst material and the inert material may be combined as portions of the same particles and/or may be separate particles. Additionally, the catalyst material and/or inert material may be essentially spherical (i.e., <about 20%, <about 30%, <about 40%, <about 50% aberration in diameter).

Suitable amounts of inert material in the particulate material may be about 0.0 wt %, ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, or ≥about 99.0 wt %. Additionally or alternatively, the particulate material may comprise an inert material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, or ≤about 99.0 wt %. Preferably, the particulate material may comprise ≤about 30.0 wt % inert material. Ranges expressly disclosed include combinations of any of the above-enumerated values, e.g., about 0.0 wt % to about 99.0 wt %, about 0.0 wt % to about 95.0 wt %, about 10.0 wt % to about 90.0 wt %, about 20.0 wt % to about 80.0 wt %, etc. Preferably, the particulate material may comprise an inert material in an amount of about 0.0 wt % to about 95.0 wt %, more preferably about 0.0 wt % to about 90.0 wt %, more preferably about 30.0 wt % to about 85.0 wt %.

In various aspects, the catalyst material and/or the inert material (either as separate particles or as combined as portions of the same particles) may have an average diameter of ≥about 5 µm, ≥about 10 µm, ≥about 20 µm, ≥about 30 µm, ≥about 40 µm, ≥about 50 µm, ≥about 100 µm, ≥about 150 µm, ≥about 200 µm, ≥about 250 µm, ≥about 300 µm, ≥about 350 µm, ≥about 400 µm, ≥about 450 µm, ≥about 500 µm, ≥about 550 µm, ≥about 600 µm, ≥about 650 µm, ≥about 700 µm, ≥about 750 µm, ≥about 800 µm, ≥about 850 µm, ≥about 900 µm, ≥about 950 µm, ≥about 1000 µm, ≥about 1100 µm, ≥about 1200 µm, ≥about 1300 µm, ≥about 1400 µm, or ≥about 1500 µm. Additionally or alternatively, the catalyst material and/or the inert material (either as separate particles or as combined as portions of the same particles) may have an average diameter of ≤about 5 µm, ≤about 10 µm, ≤about 20 µm, ≤about 30 µm, ≤about 40 µm, ≤about 50 µm, ≤about 100 µm, ≤about 150 µm, ≤about 200 µm, ≤about 250 µm, ≤about 300 µm, ≤about 350 µm, ≤about 400 µm, ≤about 450 µm, ≤about 500 µm, ≤about 550 µm, ≤about 600 µm, ≤about 650 µm, ≤about 700 µm, ≤about 750 µm, ≤about 800 µm, ≤about 850 µm, ≤about 900 µm, ≤about 950 µm, ≤about 1000 µm, ≤about 1100 µm, ≤about 1200 µm, ≤about 1300 µm, ≤about 1400 µm, or ≤about 1500 µm. Ranges expressly disclosed include combinations of any of the above-enumerated values, e.g., about 5 µm to about 1500 µm, about 20 µm to about 1200 µm, about 50 µm to about 1000 µm, about 75 µm to about 850 µm, etc. Preferably, the catalyst material and/or the inert material (either as separate particles or as combined as portions of the same particles) may have an average diameter of about 25 µm to about 1200 µm, more preferably about 50 µm to about 1000 µm, more preferably about 10 µm to about 500 µm, more preferably about 30 µm to about 400 µm, more preferably about 40 µm to about 300 µm.

Preferably, the particulate material provides at least a portion of the required heat for increasing sensible heat of the feedstock and/or converting at least a portion of the acyclic $C_5$ hydrocarbons to the first effluent comprising cyclopentadiene. For example, the particulate material may provide ≥about 30%, ≥about 35%, ≥about 40%, ≥about 45%, ≥about 50%, ≥about 55%, ≥about 60%, ≥about 65%, ≥about 70%, ≥about 75%, ≥about 80%, ≥about 85%, ≥about 90%, ≥about 95%, or 100% of the required heat. Preferably, the particulate material may provide ≥about 50% of the required heat for converting at least a portion of the acyclic $C_5$ hydrocarbons to the first effluent comprising cyclopentadiene. Ranges expressly disclosed include combinations of any of the above-enumerated values; e.g., about 30% to about 100%, about 40% to about 95%, about 50% to about 90%, etc. Preferably, the particulate material may provide about 30% to about 100% of the required heat, more preferably 50% to about 100% of the required heat, more preferably about 70% to about 100% of the required heat.

D. Effluent

An effluent (e.g., first effluent, second effluent) exiting the at least one reaction zone may comprise $H_2$ and a variety of hydrocarbon compositions produced from the reaction of the $C_5$ hydrocarbons (e.g., acyclic $C_5$ hydrocarbons) in the at least one reaction zone. The hydrocarbon compositions typically have mixtures of hydrocarbon compounds having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, the first effluent comprises cyclopentadiene. The cyclopentadiene may be present in a hydrocarbon portion of an effluent (e.g., first effluent, second effluent) in an amount of ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, or ≥about 80.0 wt %. Additionally or alternatively, the cyclopentadiene may be present in a hydrocarbon portion of an effluent (e.g., first effluent, second effluent) in an amount of ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, or ≤about 85.0 wt %. Ranges expressly disclosed include combinations of any of the above-enumerated values, e.g., about 20.0 wt % to about 85.0 wt %, about 30.0 wt % to about 75.0 wt %, about 40.0 wt % to about 85.0 wt %, about 50.0 wt % to about 85.0 wt %, etc. Preferably, the cyclopentadiene may be present in a hydrocarbon portion of an effluent (e.g., first effluent, second effluent) in an amount of about 10.0 wt % to about 85.0 wt %, more preferably about 25.0 wt % to about 80.0 wt %, more preferably about 40.0 wt % to about 75.0 wt %.

In other aspects, an effluent (e.g., first effluent, second effluent) may comprise one or more other $C_5$ hydrocarbons in addition to cyclopentadiene. Examples of other $C_5$ hydrocarbons include, but are not limited to cyclopentane and cyclopentene. The one or more other $C_5$ hydrocarbons may be present in a hydrocarbon portion of an effluent (e.g., first effluent, second effluent) in an amount of ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, or ≥about 70.0 wt %. Additionally or alternatively, the one or more other $C_5$ hydrocarbons may be present in a hydrocarbon portion of an effluent (e.g., first effluent, second effluent) in an amount of ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, or ≤about 70.0 wt %. Ranges expressly disclosed include combinations of any of the above-enumerated values, e.g., about 1.0 wt % to about 70.0 wt %, about 10.0 wt % to about 55.0 wt %, about 15.0 wt % to about 60.0 wt %, about 25.0 wt % to about 65.0 wt %, etc. Preferably, the one or more other $C_5$ hydrocarbons may be present in a hydrocarbon portion of an effluent (e.g., first effluent, second effluent) in an amount of about 30.0 wt % to about 65.0 wt %, more preferably about 20.0 wt % to about 40.0 wt %, more preferably about 10.0 wt % to about 25.0 wt %.

In other aspects, an effluent (e.g., first effluent, second effluent) may also comprise one or more aromatics, e.g., having 6 to 30 carbon atoms, particularly 6 to 18 carbon atoms. The one or more aromatics may be present in a hydrocarbon portion of an effluent (e.g., first effluent, second effluent) in an amount of about ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, or ≥about 65.0 wt %. Additionally or alternatively, the one or more aromatics may be present in a hydrocarbon portion of an effluent (e.g., first effluent, second effluent) in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, or ≤about 65.0 wt %. Ranges expressly disclosed include combinations of any of the above-enumerated values, e.g., about 1.0 wt % to about 65.0 wt %, about 10.0 wt % to about 50.0 wt %, about 15.0 wt % to about 60.0 wt %, about 25.0 wt % to about 40.0 wt %, etc. Preferably, the one or more aromatics may be present in a hydrocarbon portion of an effluent (e.g., first effluent, second effluent) in an amount of about 1.0 wt % to about 15.0 wt %, more preferably about 1.0 wt % to about 10.0 wt %, more preferably about 1.0 wt % to about 5.0 wt %.

For information on possible dispositions of the effluent(s), please see applications:
1) U.S. Ser. No. 62/250,678, filed Nov. 4, 2015;
2) U.S. Ser. No. 62/250,692, filed Nov. 4, 2015;
3) U.S. Ser. No. 62/250,702, filed Nov. 4, 2015; and
4) U.S. Ser. No. 62/250,708, filed Nov. 4, 2015; which are incorporated herein by reference.

E. Stripping/Separation of the Effluent

In various aspects, the particulate material may become entrained with hydrocarbons (e.g., cyclopentadiene) in the effluent (e.g., first effluent, second effluent) as the effluent travels through and/or exits the at least one reaction zone. Thus, the process may further comprise separating particulate material, which may be entrained with hydrocarbons (e.g., cyclopentadiene) in the effluent (e.g., first effluent, second effluent). This separating may comprise removal of the particulate material from the hydrocarbons (e.g., cyclopentadiene) by any suitable means, such as, but not limited to cyclones, filters, electrostatic precipitators, heavy liquid contacting, and/or other gas solid separation equipment, which may be inside and/or outside the at least one reaction zone. The effluent free of particulate material may then travel to a product recovery system. Additionally, the removed particulate material may then be fed back into the at least one reaction zone, for example, in a substantially top portion of the at least one reaction zone using known methods.

In various aspects, the hydrocarbons (e.g., cyclopentadiene) may become entrained with particulate material as the particulate material travels through and/or exits the at least one reaction zone. The hydrocarbons can be adsorbed onto and/or within the particles, as well as in the interstitial areas between the particles. Thus, the process may further comprise stripping and/or separating hydrocarbons from the particulate material in the effluent. This stripping and/or separating may comprise removal of the hydrocarbons (e.g., cyclopentadiene and/or acyclic $C_5$'s) from the particulate material by any suitable means, such as, but not limited to stripping with a gas such as $H_2$ or methane, and/or other gas solid separation equipment, which may be inside and/or outside the at least one reaction zone. The particulate material with reduced level of hydrocarbons may then travel to a reheating zone, a rejuvenation zone, and/or regeneration zone, and the hydrocarbons stripped from the particulate material may be directed to the product recovery system or to the reactor system.

F. Reheating/Rejuvenation Zone

As the reaction occurs in the at least one reaction zone, coke material may form on the particulate material, particularly on the catalyst material, which may reduce the activity of the catalyst material. Additionally or alternatively, the particulate material may cool as the reaction occurs. The catalyst material exiting the at least one reaction zone is referred to as "spent catalyst material." This spent catalyst material may not necessarily be a homogenous mix of particles as individual particles may have had a distribution of total aging in the system, time since last regeneration, and/or ratio of times spent in reaction zones relative to in the reheat/rejuvenation zones.

Thus, at least a portion of the particulate material (e.g., spent catalyst material) may be transferred from the at least one reaction zone to a reheating zone. The transferring of the particulate material (e.g., spent catalyst material) from the at least one reaction zone to a reheating zone may occur after the particulate material has been stripped and/or separated from the hydrocarbons in the reactor effluent. The reheating zone may include one more heating devices, such as, but not limited to a heating coil and/or a fired tube.

In various aspects, in the reheating zone, the particulate material (e.g., spent catalyst material) may be contacted with a rejuvenation stream (such as a hydrogen stream) to remove at least a portion of incrementally deposited coke material on the catalyst material thereby forming a rejuvenated catalyst material and a volatile hydrocarbon, such as, but not limited to methane. As used herein, the term "incrementally deposited" coke material refers to an amount of coke material that is deposited on the catalyst material during each pass of the catalyst material through the at least one reaction zone as opposed to a cumulative amount of coke material deposited on the catalyst material during multiple passes through the at least one reaction zone. Preferably, the rejuvenation stream (e.g., the hydrogen stream) is substantially free of oxygen, which can damage and/or reduce activity of the catalyst material. Preferably, the rejuvenation stream comprises hydrogen and is substantially free of reactive oxygen-containing compounds. "Substantially free" used in this context means the rejuvenation stream comprises less than about 1.0 wt %, based upon the weight of the rejuvenation stream, e.g., less than about 0.1 wt %, less than about 0.01 wt %, less than about 0.001 wt %, less than about 0.0001 wt %, less than about 0.00001 wt % oxygen-containing compounds. "Reactive oxygen-containing compounds" are compounds where the oxygen is available to react with the catalyst as compared to inert compounds containing oxygen (such as CO) which do not react with the catalyst. The rejuvenated catalyst material may then be returned to the at least one reaction zone.

The rejuvenation stream comprises ≥50 wt % $H_2$, such as ≥60 wt %, ≥70 wt %, preferably ≥90 wt % $H_2$. Rejuvenation gas may further comprise an inert substance (e.g., $N_2$, CO), and/or methane.

The reheating zone (i.e., the temperature to which the particulate material is exposed) may be operated at a temperature of ≥about 400° C., ≥about 450° C., ≥about 500° C., ≥about 550° C., ≥about 600° C., ≥about 650° C., ≥about 700° C., ≥about 750° C., or ≥about 800° C. Additionally or alternatively, the reheating zone may be operated at a temperature of ≤about 400° C., ≤about 450° C., ≤about 500° C., ≤about 550° C., ≤about 600° C., ≤about 650° C., ≤about 700° C., ≤about 750° C., ≤about 800° C. or ≤about 850° C. Ranges of temperatures expressly disclosed include combinations of any of the above-enumerated values, e.g., about 400° C. to about 600° C., about 450° C. to about 850° C., about 500° C. to about 800° C., etc. Preferably, the reheating zone may be operated at a temperature of about 400° C. to about 800° C., more preferably about 600° C. to about 750° C., more preferably about 550° C. to about 800° C., more preferably about 550° C. to about 700° C.

Additionally or alternatively, the reheating zone may be operated at a pressure of ≥about 1.0 psia, ≥about 5.0 psia, ≥about 25.0 psia, ≥about 50.0 psia, ≥about 75.0 psia, ≥about 100.0 psia, ≥about 125.0 psia, ≥about 150.0 psia, ≥about 175.0 psia, ≥about 200.0 psia, ≥about 225.0 psia, ≥about 250.0 psia, ≥about 275.0 psia, or ≥about 300.0 psia. Additionally or alternatively, the reheating zone may be operated at a pressure of ≤about 1.0 psia, ≤about 5.0 psia, ≤about 25.0 psia, ≤about 50.0 psia, ≤about 75.0 psia, ≤about 100.0 psia, ≤about 125.0 psia, ≤about 150.0 psia, ≤about 175.0, psia ≤about 200.0 psia, ≤about 225.0 psia, ≤about 250.0 psia, ≤about 275.0 psia, or ≤about 300.0 psia. Ranges of pressures expressly disclosed include combinations of any of the above-enumerated values, e.g., about 1.0 psia to about 300.0 psia, about 5.0 psia to about 275.0 psia, about 25.0 psia to about 250.0 psia, etc. In particular, the reheating zone may be operated at a pressure of about 1 psia to about 300 psia, more preferably about 5 psia to about 250 psia, more preferably about 25 psia to about 250 psia.

Preferably, in the reheating zone, the incrementally deposited coke material is removed from the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, or about 100.0 wt %. Preferably, at least about 10 wt %, at least about 20 wt %, at least about 50 wt %, at least about 70 wt %, or at least about 90 wt % of the incrementally deposited coke material is removed from the catalyst material. Additionally or alternatively, the incrementally deposited coke material is removed from the catalyst material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, or about 100.0 wt %. Ranges expressly disclosed include combinations of any of the above-enumerated values, e.g., about 1.0 wt % to about 100.0 wt %, about 5.0 wt % to about 95.0 wt %, about 10.0 wt % to about 90.0 wt %, about 30.0 wt % to about 90.0 wt %, etc. Preferably, the incrementally deposited coke material is removed from the catalyst material in an amount of about 1.0 wt % to about 100.0 wt %, more preferably about 10.0 wt % to about 100.0 wt %, more preferably about 60.0 wt % to about 100.0 wt %, more preferably about 90.0 wt % to about 100.0 wt %.

In various aspects, the temperature of the rejuvenated catalyst material may be ≥about 400° C., ≥about 450° C., ≥about 500° C., ≥about 550° C., ≥about 600° C., ≥about 650° C., ≥about 700° C., ≥about 750° C., or ≥about 800° C. Additionally or alternatively, the temperature of the rejuvenated catalyst material may be ≤about 400° C., ≤about 450° C., ≤about 500° C., ≤about 550° C., ≤about 600° C., ≤about 650° C., ≤about 700° C., ≤about 750° C., ≤about 800° C., or ≤about 850° C. Ranges of temperatures expressly disclosed include combinations of any of the above-enumerated values, e.g., about 400° C. to about 800° C., about 450° C. to about 850° C., about 500° C. to about 800° C., etc. Preferably, the temperature of the rejuvenated catalyst material may be of about 400° C. to about 700° C., more preferably about 500° C. to about 750° C., more preferably about 550° C. to about 700° C.

In one embodiment, the reheating zone may include multiple fluid bed tubes placed inside a fire box (or furnace). The fire box may include a radiant section, a shield, and a convection section. Fuel, which may comprise $H_2$, CO, light hydrocarbons ($C_1$-$C_4$), liquid hydrocarbons ($C_5$-$C_{25}$) and/or heavy liquid hydrocarbons ($C_{25+}$) and air may be introduced into a burner and fired. The radiant heat generated in the fire box may then be transferred to the tubes' walls thereby providing the heat required for heating the circulating particulate material (e.g., spent catalyst material). The convection section may be used for gas preheat and/or for making steam. The fire box may either be fired from the top or bottom. The flue gas may flow in a direction cross-current, co-current or counter-current to a direction of flow of the particulate material (e.g., spent catalyst material) circulating inside the multiple fluid bed tubes. Additionally, hydrogen gas may be used to lift and fluidize the particulate material (e.g., spent catalyst material) circulating inside the multiple fluid bed tubes. The hydrogen gas may either flow in a direction co-current or counter-current to a direction of flow of the particulate material (e.g., spent catalyst material).

In another embodiment, the reheating zone may include multiple fluid bed tubes placed inside an enclosure wherein the tubes may be contacted with hot combustion gasses so that the tubes may be convectively heated with hot gas that is the product of combustion from a furnace, gas turbine, or catalytic combustion. The use of convective heating may reduce the film temperature to which the particulate material is exposed thereby reducing the potential for catalyst damage due to overheating. The hot combustion gas may either flow in a direction cross-current, co-current, or counter-current to a direction of flow of the particulate material (e.g., spent catalyst material) circulating inside the multiple fluid bed tubes. Additionally, hydrogen gas may be used to lift and fluidize the particulate material (e.g., spent catalyst material) circulating inside the multiple fluid bed tubes. The hydrogen gas may either flow in a direction co-current or counter-current to a direction of flow of the particulate material (e.g., spent catalyst material).

In another embodiment, the reheating zone may include a fluid bed equipped with multiple fired tubes or coils. Each coil or fired tube may be individually or commonly fired with fuel and air to provide radiant heat that may be transferred to the fluid bed through the walls. Thus, the particulate material (e.g., spent catalyst material) circulating inside the fluid bed may be reheated due to heat transfer properties of the fluid bed. The particulate material (e.g., spent catalyst material) circulating inside the fluid bed may flow in a direction cross-current, co-current, or counter-current to a direction of flow of the gas in the fired tubes. Additionally, the flue gas in each of the fired tubes may exit the reheating zone and connect to a common heater that may be ducted to a convection box, which may be used for heating the feedstock, preheating in reheating zone (e.g., preheating the hydrogen stream), and making steam. The coils may contain hot combustion gasses so that the tubes are convectively heated with hot gas that is the product of combustion from a furnace, gas turbine, or catalytic combustion; alternatively the coils may contain a heat transfer media (e.g., molten or vaporized metal or salt) that has been heated elsewhere such as in a furnace.

The regime inside the reheating zone may be:
1. The particulate regime, where the superficial gas velocity is greater than minimum fluidization velocity, but below the minimum bubbling velocity;
2. The bubbling regime, where the superficial gas velocity is greater than minimum bubbling velocity, but below the minimum slugging velocity;
3. The slugging regime, where the superficial gas velocity is greater than the minimum slugging velocity, but below the transition to turbulent fluidization velocity at tube diameter and length within criteria for the onset of slugging, for instance, Stewart criteria (Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010);
4. The transition to turbulent fluidization regime, where the superficial gas velocity is greater than the transition to turbulent fluidization velocity, but below the fast fluidization velocity; or
5. The fast-fluidization regime, where the superficial gas velocity is greater than the fast fluidization velocity.

Preferably, the reheating zone is operated in either regime 1 or 2, which may minimize hydrogen usage in the fluid bed, maximize the catalyst material residence time for coke removal, and/or improve heat transfer properties.

In another embodiment, the particulate material (e.g., spent catalyst material) may be reheated by direct contact with a hot gas stream, which has been heated in another device, such as, a furnace, and which may be effective for coke removal (i.e., $H_2$) or at least does not result in additional coke deposition (e.g., methane).

Additionally or alternatively, rejuvenated catalyst material may be separated from the hydrogen gas and/or volatile hydrocarbon in one or multiple separation steps inside or outside the reheating zone by any suitable means, such as, but not limited to cyclones.

Additionally or alternatively, fresh particulate material may be provided directly to the at least one reaction zone and/or to the reheating zone before entering the at least one reaction zone.

G. Regeneration Zone

The process may further comprise a regeneration step to recapture catalyst activity lost due to the accumulation of coke material and/or agglomeration of metal on the catalyst material during the reaction. This regeneration step may be carried out when there has not been sufficient removal of the coke material from the particulate material (e.g., spent catalyst material) in the reheating zone. Advantageously, the regeneration step allows for substantially constant removal and addition of particulate material to the at least one reaction zone, thereby maintaining continuous operation with high catalyst activity. For example, catalyst activity in the at least one reaction zone may maintain above about 10% of the fresh catalyst activity, preferably above about 30% of the fresh catalyst activity, and most preferably above about 60% and below about 99.9% of the fresh catalyst activity.

Preferably, in the regeneration step, at least a portion of the particulate material from the at least one reaction zone or reheat zone may be transferred to a regeneration zone and regenerated by methods known in the art.

Catalyst may be continuously withdrawn from and returned to the reaction zone and/or the reheating/rejuvenation zone or may be periodically withdrawn from and returned to the reaction zone and/or reheating/rejuvenation zone. For a periodic method, typically, the regeneration times between when withdrawals are made for coke burn, purge, and reduction occur, are between about 24 hours (about 1 day) to about 240 hours (about 10 days), preferably between about 36 hours (about 1.5 days) to about 120 hours (about 5 days). Alternatively for continuous mode, the removal/addition of particulate material rate may vary between about 0.0 wt % to about 100 wt % per day, such as between about 0.1 wt % to about 100 wt % per day, of the particulate material inventory, and preferably between about 0.25 wt % to about 30.0 wt % per day of the particulate material inventory where there is balanced addition/removal of particulate material. Regeneration of the catalyst material may occur as a continuous process or may be done batch wise; in both cases intermediate vessels for inventory accumulation and/or inventory discharge may be required.

The removal and addition of the particulate material (e.g., spent catalyst, fresh particulate material, regenerated catalyst material) may occur at the same or different location in the reactor system. The particulate material (e.g., fresh particulate material, regenerated catalyst material) may be added after or before the reheating zone, while the removal of the particulate material (e.g., spent catalyst material) may be done before or after the particulate material (e.g., spent catalyst material) is passed through the reheating zone. At least a portion of the regenerated catalyst material may be recycled to the at least one reaction zone and/or at least one reheating zone. Preferably, the regenerated catalyst material and/or fresh particulate material are provided to the reheating zone to minimize any loss in heat input and to remove any remaining species that may be carried by the regenerated catalyst material from the regeneration zone. Additionally or alternatively, separators inside or outside of the regeneration zone may be used to separate the inert material from the catalyst material prior to regeneration so that just the catalyst material is regenerated. This separation may be carried out on the basis of size, magnetic, and/or density property differences between the inert material and the regenerated catalyst material using any suitable means.

Additionally or alternatively, the at least one reaction zone may comprise at least a first reaction zone, a second reaction zone, a third reaction zone, a fourth reaction zone, a fifth reaction zone, a sixth reaction zone, a seventh reaction zone, and/or an eighth reaction zone, etc. As understood herein, each reaction zone may be an individual reactor or a reactor may comprise one or more of the reaction zones. Preferably, the reactor system includes 1 to 20 reaction zones, more preferably 1 to 15 reaction zones, more preferably 2 to 10 reaction zones, more preferably 2 to 8 reaction zones. Where the at least one reaction zone may include a first and a second reaction zone, the reaction zones may be arranged in any suitable configuration, e.g., parallel or series, preferably in parallel with a common supply of feedstock and particulate material; as well as common offtake of effluent and spent particulate material. Each reaction zone, independently, may be a circulating fluidized bed reactor, preferably operated as a riser reactor. The first and second reaction zone connected in parallel may be fed by the same feedstock and/or particulate material. Additionally, the first and second reaction zone connected in parallel may provide spent catalyst material and obtain rejuvenated and/or regenerated catalyst material from the same reheating zone and/or regeneration zone.

For the above-described processes, standpipes, well known by those skilled in the art with the particle size and operating conditions described above, may be used to provide the means of transporting the particulate material between the at least one reaction zone, reheating zone, and/or regeneration zone. Slide valves and lifting gas, known by those skilled in the art, may also be used to help circulate the particulate material and/or build the necessary pressure profile inside the regeneration zone. The lifting gas may be the same as the fluidizing gas used in the reheating zone, e.g., a hydrogen stream that may contribute in minimizing the hydrogen usage in the reaction system while also reducing the coke material formation.

II. Reaction Systems for Conversion Acyclic $C_5$

In another embodiment, a reaction system 1 for converting $C_5$ hydrocarbons (e.g., acyclic $C_5$ hydrocarbons) to cyclopentadiene is provided, as shown in FIG. 1. The reaction system 1 may comprise a feedstock stream 2 comprising $C_5$ hydrocarbons (e.g., acyclic $C_5$ hydrocarbons) as described above, a first effluent stream 3 comprising cyclopentadiene, at least one catalyst stream 4 comprising a particulate material comprising a catalyst material as described above; at least one spent catalyst stream 5 comprising spent catalyst material as described above, and at least one reactor 6 as described above. The at least one reactor 6 may comprise a feedstock inlet (not shown) for providing the feedstock stream 2 to the reaction system 1; at least one catalyst inlet (not shown) for providing the at least one catalyst stream 4 to the reaction system 1; an effluent outlet (not shown) for removal of the first effluent system 3; and a spent catalyst outlet (not shown) for removal of the at least one spent catalyst system 5. Additionally or alternatively, the reaction system 1 may further comprise a hydrogen system 7 in fluid connection with the at least one reactor 6.

The at least one reactor 6 may be a circulating fluidized bed reactor, preferably a circulating fluidized bed reactor operating as a riser reactor as described above. Preferably, the at least one reactor 6 may include one or more internal structures (not shown) as described above. Particularly, the at least one reactor 6 may include a plurality of internal structures (e.g., 2, 3, 4, 5, 6, 7, 8, 9, 10, 15, 20, 30, 40, 50, etc.).

The at least one reactor 6 is operated under reaction conditions as described above to convert at least a portion of the $C_5$ hydrocarbons (e.g., acyclic $C_5$ hydrocarbons) to cyclopentadiene. Preferably, the feedstock stream 2 in the reactor 6 flows co-current to a direction of a flow of the at least one catalyst stream 4 in the reactor. Additionally, it is preferable that the at least one reactor 6 has a substantially isothermal temperature profile as described above. In particular, the feedstock stream 2 at the feedstock inlet may have a temperature of less than about 500° C. and/or the first effluent stream 3 at the effluent outlet has a temperature of at least about 550° C. Additionally, the reaction conditions may comprise a temperature of about 450° C. to about 800° C. and/or a pressure of about 3 psia to about 80 psia. Preferably, at least about 30 wt % of the acyclic $C_5$ hydrocarbons is converted to cyclopentadiene. Optionally, the at least one reactor 6 may include one or more heating devices (e.g., fired tube, heated coil) (not shown) in order to maintain temperature therein.

Particularly, the particulate material comprises at least about 30.0 wt % catalyst material as described above and further comprises an inert material as described above (e.g., less than or equal about 30.0 wt %). The catalyst material and/or the inert material may have an average diameter as described above (e.g., about 50 μm to about 1,000 μm). Preferably, the catalyst material comprises platinum on ZSM-5, platinum on zeolite L, and/or platinum on silica, preferably platinum on ZSM-5. Additionally, the particulate material may provide at least a portion (e.g., at least about 50%) of the heat required for increasing the temperature of the feedstock stream 2 and/or converting the $C_5$ hydrocarbons (e.g., acyclic $C_5$ hydrocarbons) to cyclopentadiene.

Additionally, the reaction system 1 may further comprise a cyclone 8 (one is shown, but two or more operating in series may be present with one or more operating in parallel) for separating the particulate material, which may be entrained with hydrocarbons (e.g. cyclopentadiene) in the first effluent stream 3. A second effluent stream 9 substantially free of particulate material may then travel to a product recovery system. A hydrogen stripping stream 10 may be provided to the cyclone 8. Additionally, the reaction system 1 may further comprise a first hydrogen lift gas stream 11 to help transport the at least one catalyst stream 4 into the at least one reactor 6.

Figure 2:
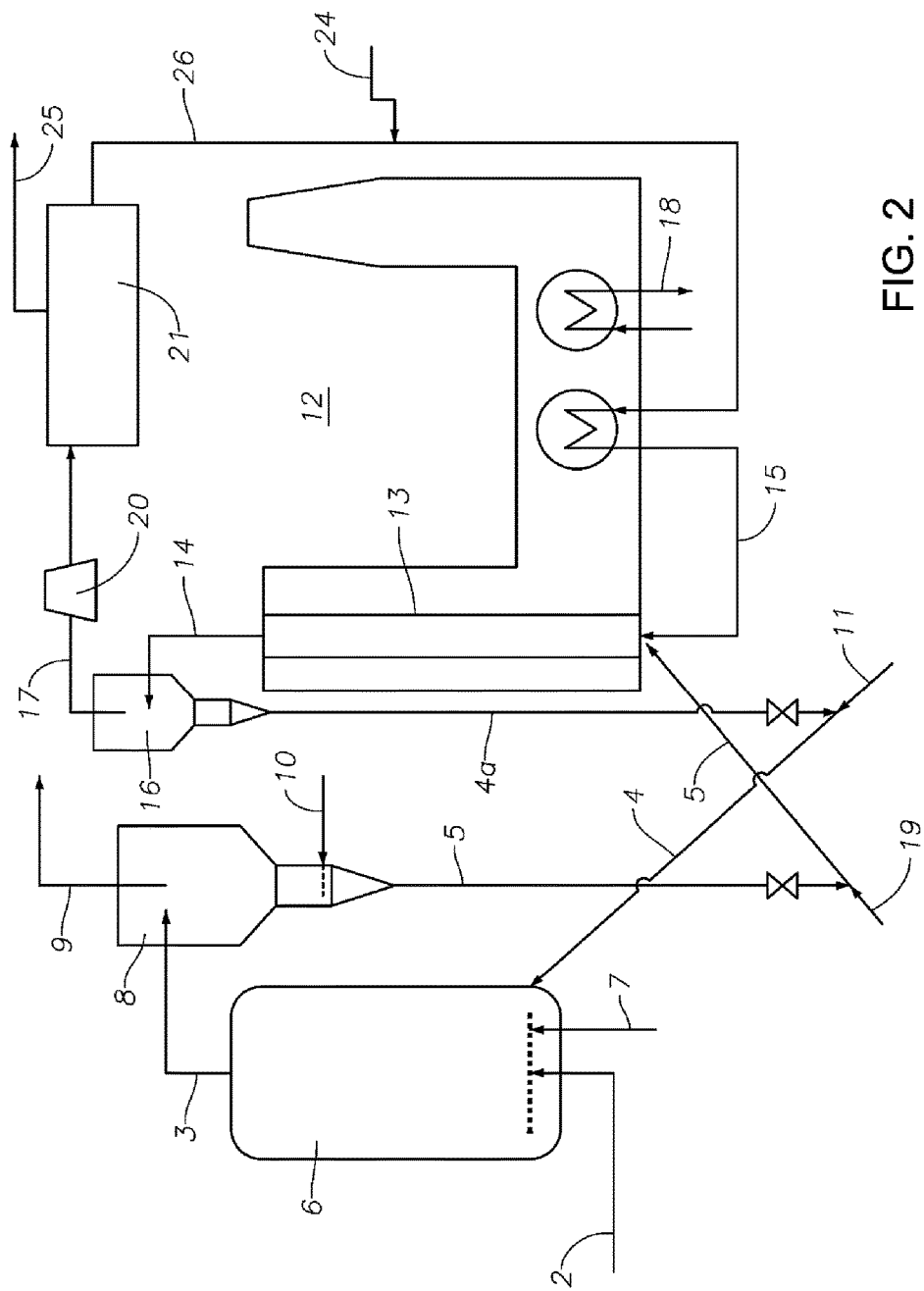
FIG. 2 is a diagram of a reactor system with a reheating apparatus according to another embodiment of the invention.

In another embodiment, the reaction system 1 may further comprise a reheating apparatus 12 for reheating and/or restoring activity of the spent catalyst material, wherein the reheating apparatus 12 is in fluid connection with the at least one reactor 6, as shown in FIG. 2. The reheating apparatus 12 may comprise one or more heating devices as described above, a reheating inlet (not shown) for the at least one spent catalyst stream 5, a means 13 for contacting the at least one spent catalyst stream 5 with hydrogen to remove at least a portion of incrementally deposited coke material on the spent catalyst material thereby forming a rejuvenated catalyst material as described above and a volatile hydrocarbon (e.g., methane), and a rejuvenation outlet (not shown) for returning a rejuvenated catalyst material stream 14 to the at least one reactor 6. The means 13 for contacting the at least one spent catalyst stream 5 with a heated hydrogen stream 15 may include any suitable means known in the art, for example, multiple fluid bed tubes placed inside a fire box or a furnace as described above, a fluid bed equipped with multiple fired tubes or coils, or multiple fluid bed tubes placed inside an enclosure wherein the tubes may be contacted with hot combustion gasses as described above.

Additionally or alternatively, the rejuvenated catalyst material stream 14 may be fed to a separator, such as a cyclone 16, for separating the rejuvenated catalyst material from the hydrogen gas and/or volatile hydrocarbon to form a separated rejuvenated catalyst material stream 4a and/or an excess hydrogen stream 17. The separated rejuvenated catalyst material stream 4a may be provided to the at least one reactor 6 and/or may form a portion of the at least one catalyst stream 4. The excess hydrogen stream 17 may be compressed in a compressor 20 and sent to a separation apparatus 21 for separation of a portion of light hydrocarbons ($C_1$-$C_4$) from the excess hydrogen stream 17 to generate a light hydrocarbon rich stream 25 and a light hydrocarbon depleted stream 26 which may be recycled back into the reheating apparatus 12. Additionally a portion of the excess hydrogen stream 17 may be compressed in a compressor 20 and used to supply hydrogen as hydrogen stripping stream 10 and/or first hydrogen lift gas stream 11. The separation apparatus 21 may be a membrane system, adsorption system, or other known system for separation of $H_2$ from light hydrocarbons. Additionally, a make-up hydrogen stream 24 may be added to stream 26 to replace $H_2$ that has been consumed during removal of coke from the catalyst.

In particular, the reheating apparatus 12 operates under conditions described above, preferably reheating apparatus 12 has a temperature of about 550° C. to about 800° C. Further, the rejuvenated catalyst material comprises less of the incrementally deposited coke material than the spent catalyst material as described above, preferably at least about 10 wt % less of the incrementally deposited coke material than the spent catalyst material.

Additionally, the reheating apparatus 12 may produce a steam stream 18 from water. The feedstock stream 2 may also be heated in the convection section (not shown) or in a separate furnace (not shown). Also, a second hydrogen lift gas stream 19 may be provided to the reaction system 1 to help transport the spent catalyst stream 5 to the reheating apparatus 12; the second hydrogen lift gas stream 19 may be a portion of the heated hydrogen stream 15. Additionally a portion of the heated hydrogen stream 15 may be used as the first hydrogen lift gas stream 11.

Figure 3:
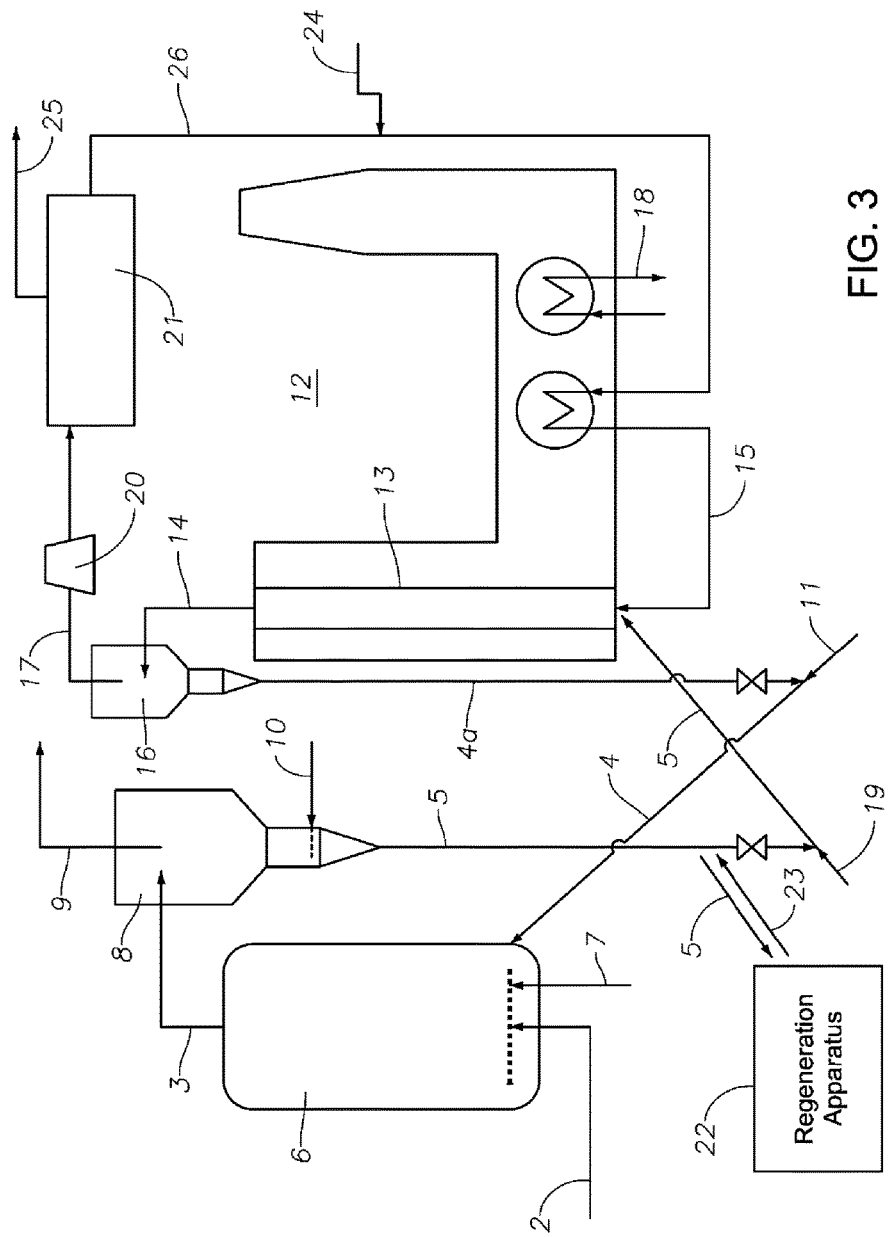
FIG. 3 is a diagram of a reactor system with a reheating apparatus and a regenerating apparatus according to another embodiment of the invention.
Figure 4:
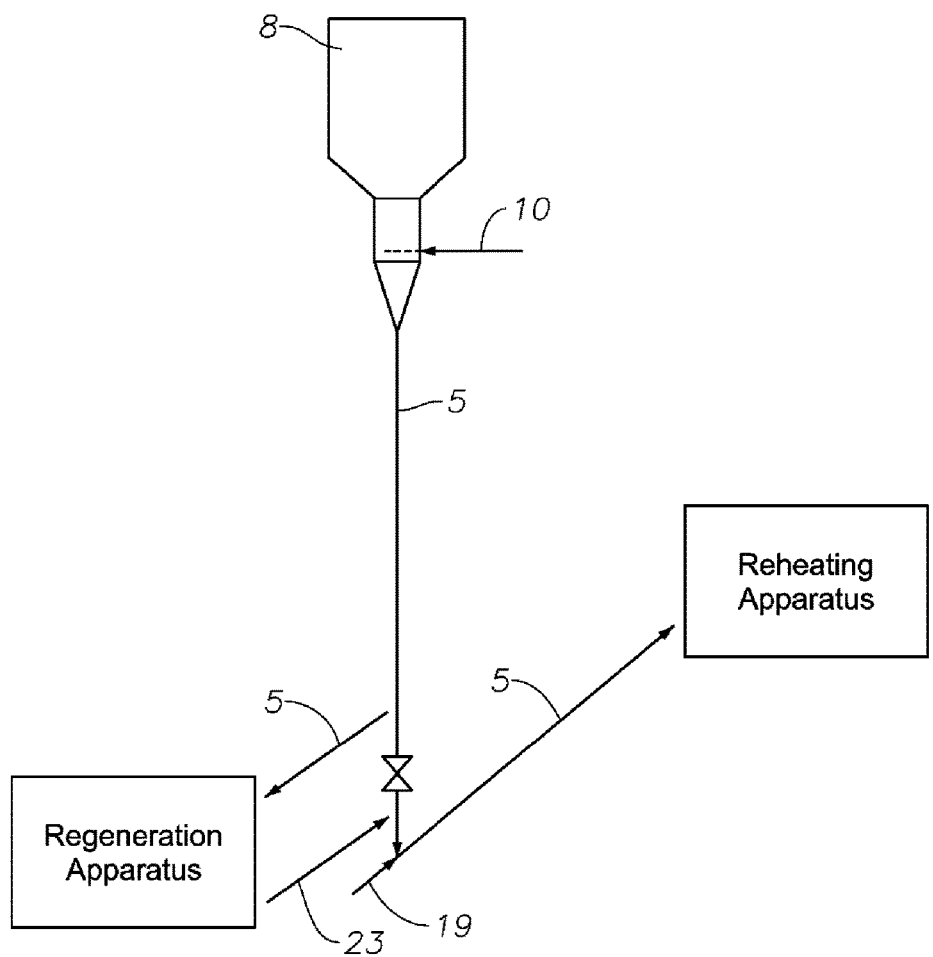
FIG. 4 is an expanded view of a spent catalyst stream in the reactor system according to another embodiment of the invention.

In another embodiment, the reaction system 1 may further comprise a regeneration apparatus 22, as known in the art, in fluid connection with the at least one reactor 6, as shown in FIG. 3, for producing regenerated catalyst material stream 23. As shown in FIG. 4, a portion of the spent catalyst stream 5 may be transferred to the reheating apparatus 12 and/or the regeneration apparatus 22. Additionally or alternatively, regenerated catalyst material stream 23 may be transferred to the reheating apparatus 12 and may enter via the reheating inlet.

Additionally or alternatively, the reaction system 1 may further comprise a fresh particulate material stream (not shown) in fluid connection with the at least one reactor 6 and/or in fluid connection with the reheating apparatus 12.

Additionally or alternatively, the at least one reactor 6 may comprise at least a first reactor, a second reactor, a third reactor, a fourth reactor, a fifth reactor, a sixth reactor, a seventh reactor, an eighth reactor, etc. As used herein, each "reactor" may be individual vessels or individual reaction zones within a single vessel. Preferably, the reaction system includes 1 to 20 reactors, more preferably 1 to 15 reactors, more preferably 2 to 10 reactors, more preferably 2 to 8 reactors. Where the at least one reactor 6 may include a first and a second reactor, the reactors may be arranged in any suitable configuration, e.g., parallel or series, preferably in parallel. Each reactor independently may be a circulating fluidized bed reactor, preferably operated as a riser reactor. The first and second reactor connected in parallel may be fed by the same feedstock and/or particulate material. Additionally, the first and second reactor connected in parallel may provide spent catalyst material and obtain rejuvenated and/or regenerated catalyst material from the same reheating apparatus 12 and/or regeneration zone 22.

IV. Further Embodiments

This invention further relates to:

Embodiment 1

A process for converting acyclic $C_5$ hydrocarbons to cyclopentadiene in a reactor system, wherein the process comprises: providing to the reactor system a feedstock comprising acyclic $C_5$ hydrocarbons; providing to the reactor system a particulate material comprising a catalyst material (e.g., platinum on ZSM-5, platinum on zeolite L, and/or platinum on silica); contacting the feedstock and the particulate material in the at least one reaction zone (e.g., circulating fluidized bed reactor) under reaction conditions to convert at least a portion of the acyclic $C_5$ hydrocarbons to a first effluent comprising cyclopentadiene; wherein the feedstock flows co-current to a direction of a flow of the particulate material.

Embodiment 2

The process of embodiment 1, wherein an isothermal temperature profile is maintained in the at least one reaction zone.

Embodiment 3

The process of embodiment 1 or 2, wherein the feedstock is provided at a temperature of less than or equal to about 500° C. and/or the first effluent exiting the at least one reaction zone has a temperature of at least about 550° C.

Embodiment 4

The process of any one of the previous embodiments, wherein the at least one reaction zone further comprises at least one heating device.

Embodiment 5

The process of any one of the previous embodiments, wherein the reaction conditions comprise a temperature of about 450° C. to about 800° C., a pressure of about 3 psia to about 80 psia, and/or at least about 30 wt % of the acyclic $C_5$ hydrocarbons is converted to cyclopentadiene.

Embodiment 6

The process of any one of the previous embodiments, wherein the particulate material further comprises an inert material (e.g., less than or equal to about 30 wt %) and/or at least about 30 wt % catalyst material.

Embodiment 7

The process of any one of the previous embodiments, wherein the catalyst material and/or the inert material has an average diameter of about 50 μm to about 1,000 μm.

Embodiment 8

The process of any one of the previous embodiments, wherein the particulate material provides at least about 50% of required heat for converting at least a portion of the acyclic $C_5$ hydrocarbons to the first effluent comprising cyclopentadiene.

Embodiment 9

The process of any one of the previous embodiments, wherein the at least one reaction zone comprises at least a first reaction zone (e.g., circulating fluidized bed) and a second reaction zone (e.g., circulating fluidized bed) connected in parallel.

Embodiment 10

The process of any one of the previous embodiments further comprising any one or more of the following: transferring at least a portion of the particulate material from the at least one reaction zone to a reheating zone (e.g., a plurality of fluid bed tubes within a furnace and/or a fluidized bed having one or more heating devices), wherein the reheating zone comprises one or more heating devices; contacting the particulate material with hydrogen to remove at least a portion of incrementally deposited coke on the catalyst material thereby forming rejuvenated catalyst material and a volatile hydrocarbon; and returning the rejuvenated catalyst material to the at least one reaction zone.

Embodiment 11

The process of embodiment 10, wherein the reheating zone is operated at a temperature of about 550° C. to about 800° C. and/or at least 10 wt % of the incrementally deposited coke material is removed from the catalyst material.

Embodiment 12

The process of any one of the previous embodiments further comprising any one or more of the following: transferring at least a portion of the particulate material from the at least one reaction zone to a regeneration zone; wherein the particulate material is contacted with a regeneration gas under regenerating conditions to oxidatively remove at least a portion of coke material deposited on the catalyst material thereby forming a regenerated catalyst material; and recycling at least a portion of the regenerated catalyst material to the at least one reaction zone or at least one reheating zone.

Embodiment 13

The process of any one of the previous embodiments further comprising feeding hydrogen to the at least one reaction zone and/or providing fresh particulate material (i) directly to the at least one reaction zone and/or (ii) to the reheating zone before entering the at least one reaction zone.

Embodiment 14

A reaction system for converting acyclic $C_5$ hydrocarbons to cyclopentadiene, wherein the reaction system comprises: a feedstock stream comprising acyclic $C_5$ hydrocarbons; a first effluent stream comprising cyclopentadiene; at least one catalyst stream comprising a particulate material comprising a catalyst material (e.g., platinum on ZSM-5, platinum on zeolite L, and/or platinum on silica); at least one spent catalyst stream comprising spent catalyst material; at least one reactor (e.g., circulating fluidized bed reactor) operated under reaction conditions to convert at least a portion of the acyclic $C_5$ hydrocarbons to cyclopentadiene; and wherein the at least one reactor comprises: a feedstock inlet for providing the feedstock stream to the reaction system; at least one catalyst inlet for providing the at least one catalyst stream to the reaction system; an effluent outlet for removal of the first effluent stream; and a spent catalyst outlet for removal of the at least one spent catalyst stream; wherein the feedstock stream in the reactor flows co-current to a direction of a flow of the at least one catalyst stream in the reactor.

Embodiment 15

The reaction system of embodiment 14, wherein the at least one reactor has a substantially isothermal profile.

Embodiment 16

The reaction system of embodiment 14 or 15, wherein the feedstock stream at the feedstock inlet has a temperature of less than about 500° C. and/or the first effluent stream at the effluent outlet has a temperature of at least about 550° C.

Embodiment 17

The reaction system of any one embodiments 14, 15, or 16, wherein the at least one reactor further comprises at least one heating device.

Embodiment 18

The reaction system of any one of embodiments 14, 15, 16, or 17, wherein the reaction conditions comprise a temperature of about 450° C. to about 800° C., a pressure of about 3 psia to about 80 psia, and/or at least about 30 wt % of the acyclic $C_5$ hydrocarbons is converted to cyclopentadiene.

Embodiment 19

The reaction system of any one of embodiments 14, 15, 16, 17, or 18, wherein the particulate material further comprises an inert material (less than or equal to about 30 wt %) and/or at least about 30 wt % catalyst material.

Embodiment 20

The reaction system of any one of embodiments 14, 15, 16, 17, 18, or 19, wherein the catalyst material and/or the inert material has an average diameter of about 50 μm to about 1,000 μm.

Embodiment 21

The reaction system of any one of embodiments 14, 15, 16, 17, 18, 19, or 20, wherein the particulate material provides at least about 50% of required heat for converting at least a portion of the acyclic $C_5$ hydrocarbons to the first effluent comprising cyclopentadiene.

Embodiment 22

The reaction system of any one of embodiments 14, 15, 16, 17, 18, 19, 20, or 21, wherein the at least one reactor comprises at least a first reactor (e.g., circulating fluidized bed) and a second reactor (e.g., circulating fluidized bed) connected in parallel.

Embodiment 23

The reaction system of any one of embodiments 14, 15, 16, 17, 18, 19, 20, 21, or 22 further comprising a reheating apparatus (e.g., a plurality of fluid bed tubes within a furnace and/or a fluidized bed having one or more heating devices) in fluid connection with the at least one reactor, wherein the reheating apparatus comprises: one or more heating devices; a reheating inlet for the at least one spent catalyst stream; a means for contacting the at least one spent catalyst stream with hydrogen to remove at least a portion of incrementally deposited coke material on the spent catalyst material thereby forming a rejuvenated catalyst material and a volatile hydrocarbon; and a rejuvenation outlet for returning a rejuvenated catalyst material stream to the at least one reactor.

Embodiment 24

The reaction system of embodiment 23, wherein the reheating apparatus has a temperature of about 550° C. to about 800° C. and/or the rejuvenated catalyst material comprises at least about 10 wt % less of the incrementally deposited coke material than the spent catalyst material.

Embodiment 25

The reaction system of any one of embodiments 14, 15, 16, 17, 18, 19, 20, 21, 22, 23, or 24 further comprising: a regeneration apparatus in fluid connection with the at least one reactor for forming a regenerated catalyst material.

Embodiment 26

The reaction system of any one of embodiments 14, 15, 16, 17, 18, 19, 20, 21, 22, 23, 24, or 25 further comprising a hydrogen stream in fluid connection with the at least one reactor and/or a fresh particulate material stream in fluid connection with the at least one reactor and/or in fluid connection with the reheating apparatus.

This invention further relates to the following embodiments 27-49:

Embodiment 27

A reaction system for converting acyclic $C_5$ hydrocarbons to cyclopentadiene, wherein the reaction system comprises:
a feedstock stream comprising acyclic $C_5$ hydrocarbons;
a first effluent stream comprising cyclopentadiene;
at least one catalyst stream comprising a particulate material comprising a catalyst material;
at least one spent catalyst stream comprising a spent catalyst material;
at least one reactor operated under reaction conditions to convert at least a portion of the acyclic $C_5$ hydrocarbons to cyclopentadiene; and wherein the at least one reactor comprises:
a feedstock inlet for providing the feedstock stream to the reaction system;
at least one catalyst inlet for providing the at least one catalyst stream to the reaction system; and
an effluent outlet for removal of the first effluent stream and the at least one spent catalyst stream;
wherein the feedstock stream in the reactor flows co-current to a direction of a flow of the at least one catalyst stream in the reactor.

Embodiment 28

The reaction system of embodiment 27, wherein the at least one reactor has a substantially isothermal temperature profile.

Embodiment 29

The reaction system of embodiment 27, wherein the at least one reactor is a circulating fluidized bed reactor.

Embodiment 30

The reaction system of embodiment 27, wherein the feedstock stream at the feedstock inlet has a temperature of less than or equal to about 500° C.

Embodiment 31

The reaction system of embodiment 27, wherein the first effluent stream at the effluent outlet has a temperature of at least about 550° C.

Embodiment 32

The reaction system of embodiment 27 further comprising:
a reheating apparatus in fluid connection with the at least one reactor, wherein the reheating apparatus comprises:
one or more heating devices;
a reheating inlet for the at least one spent catalyst stream;
a means for contacting the at least one spent catalyst stream with hydrogen to remove at least a portion of incrementally deposited coke material on the spent catalyst material thereby forming a rejuvenated catalyst material and a volatile hydrocarbon; and
a rejuvenation outlet for returning the rejuvenated catalyst material to the at least one reactor.

Embodiment 33

The reaction system of embodiment 32, wherein the reheating apparatus has a temperature of about 550° C. to about 800° C.

Embodiment 34

The reaction system of embodiment 32, wherein the rejuvenated catalyst material comprises at least about 10 wt % less of the incrementally deposited coke material than the spent catalyst material.

Embodiment 35

The reaction system of embodiment 32, where the reheating apparatus comprises a plurality of fluid bed tubes within a furnace and/or a fluidized bed having one or more heating devices.

Embodiment 36

The reaction system of embodiment 27 further comprising:
a regeneration apparatus in fluid connection with the at least one reactor for forming a regenerated catalyst material.

Embodiment 37

The reaction system of embodiment 27 further comprising a hydrogen stream in fluid connection with the at least one reactor.

Embodiment 38

The reaction system of embodiment 27, wherein the at least one reactor further comprises at least one heating device.

Embodiment 39

The reaction system of embodiment 27, wherein the reaction conditions comprise a temperature of about 450° C. to about 800° C. and a pressure of about 3 psia to about 80 psia.

Embodiment 40

The reaction system of embodiment 27, wherein at least about 30 wt % of the acyclic $C_5$ hydrocarbons is converted to cyclopentadiene.

Embodiment 41

The reaction system of embodiment 27, wherein the particulate material further comprises an inert material.

Embodiment 42

The reaction system of embodiment 41, wherein the catalyst material has an average diameter of about 50 μm to about 1,000 μm and the inert material has an average diameter of about 50 μm to about 1,000 μm.

Embodiment 43

The reaction system of embodiment 41, wherein the particulate material comprises less than or equal to about 30 wt % inert material.

Embodiment 44

The reaction system of embodiment 27, wherein the particulate material comprises at least about 30 wt % catalyst material.

Embodiment 45

The reaction system of embodiment 27, wherein the catalyst material comprises platinum on ZSM-5, platinum on zeolite L, and/or platinum on silica.

Embodiment 46

The reaction system of embodiment 27, wherein the particulate material provides at least about 50% of required heat for converting the acyclic $C_5$ hydrocarbons to cyclopentadiene.

Embodiment 47

The reaction system of embodiment 27, wherein the at least one reactor comprises at least a first reactor and a second reactor connected in parallel.

Embodiment 48

The reaction system of embodiment 27, wherein the first reaction and second reaction zones are a circulating fluidized bed reactor.

Embodiment 49

The reaction system of embodiment 32 further comprising a fresh particulate material stream in fluid connection with the at least one reactor and/or in fluid connection with the reheating apparatus.

INDUSTRIAL APPLICABILITY

The first hydrocarbon reactor effluent obtained during the acyclic $C_5$ conversion process containing cyclic, branched, and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

Scheme I

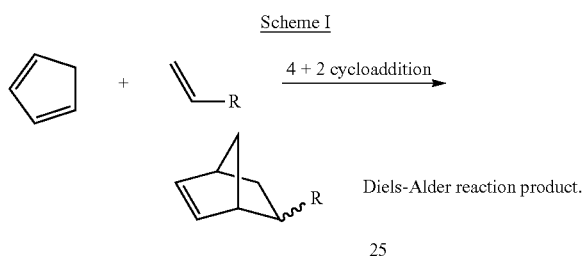

Diels-Alder reaction product.

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

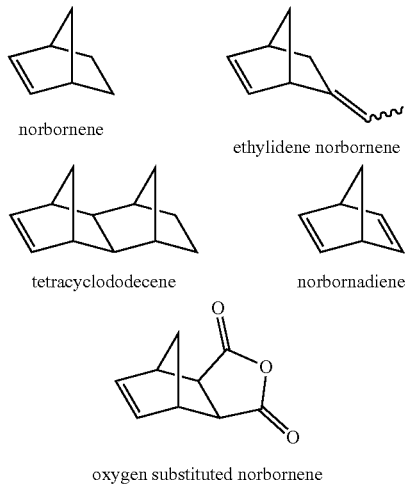

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

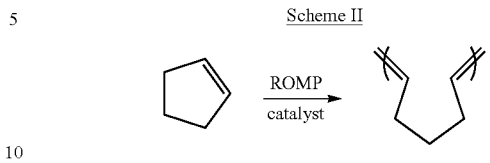

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

EXAMPLES

Example 1

A mixture with ~22% solids was prepared by mixing 8,800 g of DI water, 600 g of 50% NaOH solution, 26 g of 43% Sodium Aluminate solution, 730 g of n-propyl amine 100% solution, 20 g of ZSM-5 seed crystals, and 3,190 g of Sipernat-340 silica in a 5-gal pail container. The mixture was then charged into a 5-gal autoclave. The mixture had the following molar composition:

| | |
|---|---|
| $SiO_2/Al_2O_3$ | ~470 |
| $H_2O/SiO_2$ | ~10.7 |
| $OH/SiO_2$ | ~0.16 |
| $Na/SiO_2$ | ~0.16 |
| n-PA/Si | ~0.25. |

In the autoclave, the mixture was mixed at 350 rpm and reacted at 210° F. (99° C.) for 72 hours. The resulting reaction slurry was discharged and stored in a 5-gal pail container. The XRD pattern (not shown) of the as-synthesized material showed the typical pure phase of ZSM-5 topology. The SEM (not shown) of the as-synthesized material showed that the material was composed of a mixture of crystals with a size of 0.5-1 micron. The as-synthesized crystals had a $SiO_2/Al_2O_3$ molar ratio of ~467 and Na of ~0.25 wt %.

This material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. for 6 hours. After cooling, 0.29 wt % Ag was added via incipient wetness impregnation using an aqueous solution of silver nitrate. The sample was dried for four hours at 250° F. (120° C.). Subsequently, 0.44 wt % Pt was added via incipient wetness impregnation using an aqueous solution of tetraamine platinum hydroxide. The catalyst was dried in air at room temperature then at 250° F. (120° C.), and calcined in air for one hour at 610° F. (320° C.).

Example 2

The catalyst of Example 1 was tested under two reactor temperature profiles: a substantially isothermal temperature profile and an inverse temperature profile. The catalyst (0.5 g) was physically mixed with quartz (1.5 g, 60-80 mesh) and loaded into a ⅜" OD, 18" long stainless steel reactor. The catalyst bed was held in place with quartz wool and the reactor void space was loaded with coarse quartz particles. The catalyst was dried for 1 hour under He (100 mL/min, 30 psig, 250° C.) then reduced for 1 hour under H2 (200 mL/min, 30 psig, 500° C.). The catalyst was then tested for performance with a feed containing n-pentane, H2, and balance He.

The test conditions for maintaining an isothermal temperature profile were the following: 0.5 g ZSM-5(400:1)/ 0.4% Pt/0.2% Ag, 5 psia C5H12 at reactor inlet, 1:1 H2:C5 feed, and 60 psia total pressure with He balance, WHSV was 16.1 h-1, 600° C. bed temperature. The test conditions for maintaining an inverse temperature profile were the following: 0.5 g ZSM-5(400:1)/0.4% Pt/0.2% Ag, 5 psia C5H12 at reactor inlet, 1:1 H2:C5 feed, and 60 psia total pressure with He balance, WHSV was 4.0 h-1 for the gradient experiment and a linear temperature gradient of 500 to 600° C. was applied. The performance results of Example 2 are shown in FIGS. 5 and 6.

Figure 5:
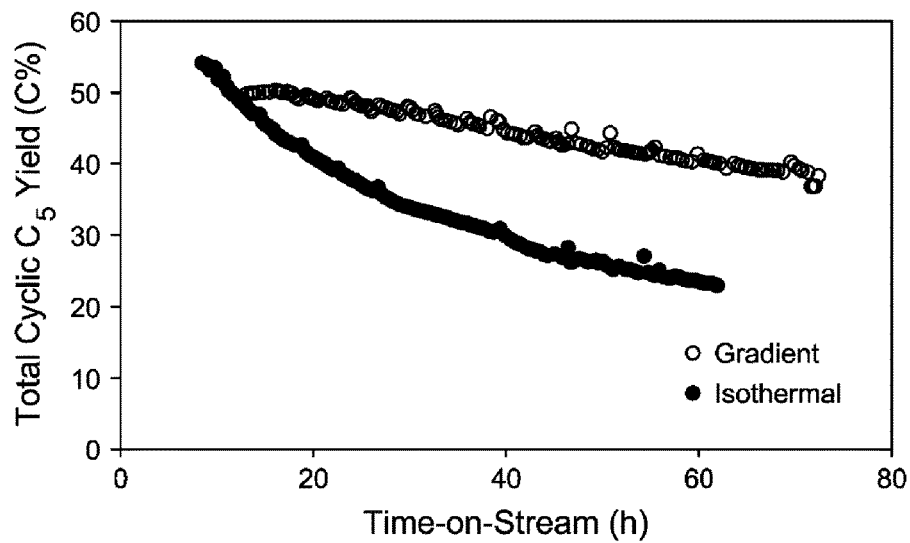
FIG. 5 illustrates the total carbon yield of cyclic $C_5$ hydrocarbons against time on stream (T.O.S.) in Example 2, while maintaining an inverse temperature profile (500 to 600° C. over 6 inches) or an isothermal temperature profile (600° C. throughout the 6 inches).
Figure 6:
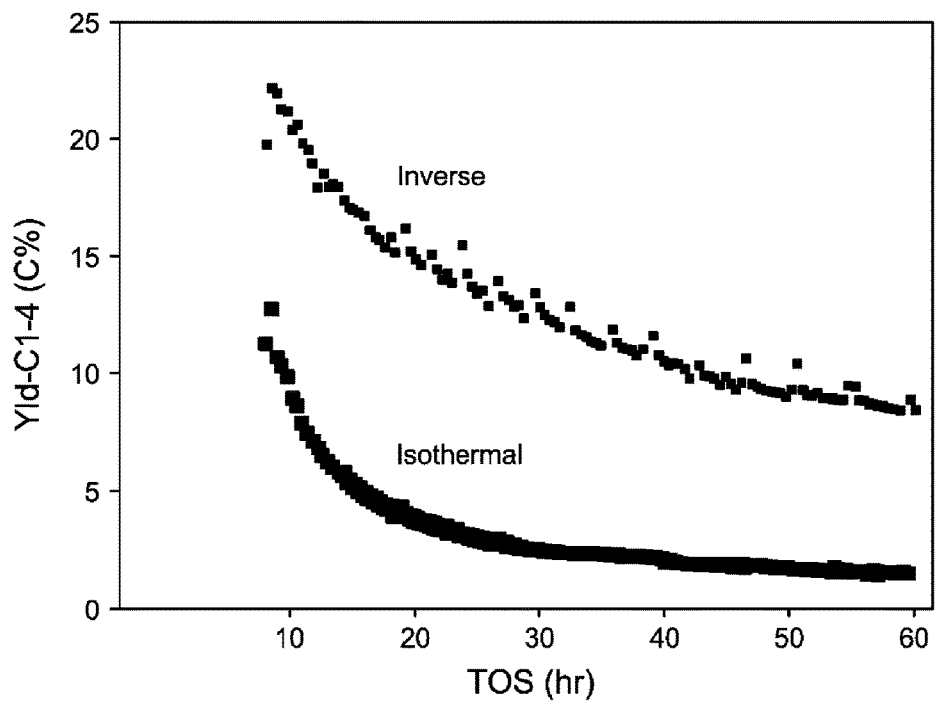
FIG. 6 illustrates the total carbon yield of $C_1$-$C_4$ hydrocarbons against T.O.S. in Example 2, while maintaining an inverse temperature profile (500 to 600° C. over 6 inches) or an isothermal temperature profile (600° C. throughout the 6 inches).

As shown in FIG. 5, a reactor operating with an inverse or gradient temperature profile (i.e., a lower temperature at the inlet and a higher temperature at the outlet), results in a catalyst having higher stability over that of a reactor operating isothermally at the same outlet temperature. Specifically, FIG. 5 shows that while the total cyclic $C_5$ hydrocarbon yield for both temperature profiles was similar initially, the yield decreased to 43% of its original value over 53 hours in the reactor having an isothermal temperature profile. In contrast, the yield in an inverse temperature profile operating regime only decreased to 73% of its original value, and this decline in yield occurred over a longer timeframe of 57 hours. As shown in FIG. 6, a reactor operating isothermally can be beneficial over that operating regime with an inverse or gradient temperature profile when it is desired to minimize the yield of byproduct $C_1$-$C_4$ cracked hydrocarbon products.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for converting acyclic $C_5$ hydrocarbons to cyclic $C_5$ compounds including cyclopentadiene in a reactor system, wherein the process comprises:
   providing to the reactor system a feedstock comprising acyclic $C_5$ hydrocarbons;
   providing to the reactor system a particulate material comprising a catalyst material;
   contacting the feedstock and the particulate material in at least one reaction zone under reaction conditions to convert at least a portion of the acyclic $C_5$ hydrocarbons to a first effluent comprising cyclopentadiene; and
   wherein the feedstock flows co-current to a direction of a flow of the particulate material.

2. The process of claim 1, wherein an isothermal temperature profile is maintained in the at least one reaction zone.

3. The process of claim 1, wherein the at least one reaction zone is a circulating fluidized bed reactor.

4. The process of claim 1, wherein the feedstock is provided at a temperature of less than or equal to about 500° C.

5. The process of claim 1, wherein the first effluent exiting the at least one reaction zone has a temperature of at least about 550° C.

6. The process of claim 1 further comprising: transferring at least a portion of the particulate material from the at least one reaction zone to a reheating zone, wherein the reheating zone comprises one or more heating devices.

7. The process of claim 6 further comprising:
   contacting the particulate material with hydrogen to remove at least a portion of incrementally deposited coke material on the catalyst material thereby forming rejuvenated catalyst material and a volatile hydrocarbon; and
   returning the rejuvenated catalyst material to the at least one reaction zone.

8. The process of claim 7, wherein the reheating zone is operated at a temperature of about 550° C. to about 800° C.

9. The process of claim 7, wherein at least 10 wt % of the incrementally deposited coke material is removed from the catalyst material.

10. The process of claim 7, wherein the reheating zone comprises a plurality of fluid bed tubes within a furnace and/or a fluidized bed having one or more heating devices.

11. The process of claim 6 further comprising:
   transferring at least a portion of the particulate material from the at least one reaction zone to a regeneration zone; wherein the particulate material is contacted with a regeneration gas under regenerating conditions to oxidatively remove at least a portion of coke material deposited on the catalyst material thereby forming a regenerated catalyst material; and
   recycling at least a portion of the regenerated catalyst material to the at least one reaction zone or the reheating zone.

12. The process of claim 1 further comprising feeding hydrogen to the at least one reaction zone.

13. The process of claim 1, wherein the at least one reaction zone comprises at least one heating device.

14. The process of claim 1, wherein the reaction conditions comprise a temperature of about 450° C. to about 800° C. and a pressure of about 3 psia to about 80 psia.

15. The process of claim 1, wherein at least about 30 wt % of the acyclic $C_5$ hydrocarbons is converted to cyclopentadiene.

16. The process of claim 1, wherein the particulate material further comprises an inert material.

17. The process of claim 16, wherein the catalyst material has an average diameter of about 50 μm to about 1,000 μm and the inert material has an average diameter of about 50 μm to about 1,000 μm.

18. The process of claim 16, wherein the particulate material comprises less than or equal to about 30 wt % inert material.

19. The process of claim 1, wherein the particulate material comprises at least about 30 wt % catalyst material.

20. The process of claim 1, wherein the catalyst material comprises platinum on ZSM-5, platinum on zeolite L, and/or platinum on silica.

21. The process of claim 1, wherein the particulate material provides at least about 50% of required heat for converting at least a portion of the acyclic $C_5$ hydrocarbons to the first effluent comprising cyclopentadiene.

22. The process of claim 1, wherein the at least one reaction zone comprises at least a first reaction zone and a second reaction zone operated in parallel.

23. The process of claim 22, wherein the first reaction and second reaction zones are a circulating fluidized bed reactor.

24. The process of claim 6 further comprising providing fresh particulate material (i) directly to the at least one reaction zone and/or (ii) to the reheating zone before entering the at least one reaction zone.

\* \* \* \* \*